(12) United States Patent
Ruiz-Lozano et al.

(10) Patent No.: US 10,149,922 B1
(45) Date of Patent: Dec. 11, 2018

(54) ENGINEERED COLLAGEN MATRICES FOR MYOCARDIAL THERAPY

(71) Applicants: The Board of Trustees of the Leland Stanford Junior University, Palo Alto, CA (US); Sanford-Burnham Medical Research Institute, La Jolla, CA (US)

(72) Inventors: Pilar Ruiz-Lozano, Los Altos, CA (US); Vahid Serpooshan, Berkeley, CA (US); Mingming Zhao, Sunnyvale, CA (US); Daniel Bernstein, Palo Alto, CA (US); Mark Mercola, Rancho Santa Fe, CA (US); Ke Wei, San Diego, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 457 days.

(21) Appl. No.: 14/168,826

(22) Filed: Jan. 30, 2014

Related U.S. Application Data

(63) Continuation of application No. 14/062,385, filed on Oct. 24, 2013, now abandoned.

(60) Provisional application No. 61/718,046, filed on Oct. 24, 2012.

(51) Int. Cl.
| | |
|---|---|
| *A61L 17/08* | (2006.01) |
| *A61L 27/36* | (2006.01) |
| *A61L 27/22* | (2006.01) |
| *A61L 27/24* | (2006.01) |
| *A61L 27/50* | (2006.01) |

(52) U.S. Cl.
CPC ......... *A61L 27/3625* (2013.01); *A61L 27/227* (2013.01); *A61L 27/24* (2013.01); *A61L 27/50* (2013.01)

(58) Field of Classification Search
CPC .......... A61K 9/70; A61K 35/12; A61K 35/17; A61K 35/34; A61K 35/44
USPC .................................................. 424/465–50
See application file for complete search history.

(56) References Cited

U.S. PATENT DOCUMENTS

| | | | |
|---|---|---|---|
| 6,306,169 B1 | 10/2001 | Lee et al. | |
| 6,572,650 B1* | 6/2003 | Abraham ................. | A61L 27/24 623/1.38 |
| 6,627,615 B1 | 9/2003 | Debs et al. | |
| 2003/0022367 A1 | 1/2003 | Xu | |
| 2005/0013870 A1* | 1/2005 | Freyman ............. | A61L 27/3633 424/520 |
| 2005/0164345 A1 | 7/2005 | Kivirikko et al. | |
| 2007/0065415 A1* | 3/2007 | Kleinsek ................. | A61K 35/12 424/93.7 |
| 2008/0004713 A1* | 1/2008 | Nakamura .......... | A61L 27/3633 623/23.72 |
| 2008/0131473 A1 | 5/2008 | Brown et al. | |
| 2008/0241866 A1 | 10/2008 | Korlach et al. | |
| 2010/0184183 A1* | 7/2010 | Schussler ................ | A61L 27/24 435/177 |
| 2010/0196441 A1 | 8/2010 | Sondermeijer et al. | |
| 2011/0189140 A1* | 8/2011 | Christman ............. | A61K 35/34 424/93.7 |
| 2011/0206619 A1 | 8/2011 | Mahmoudi et al. | |
| 2012/0034164 A1 | 2/2012 | Ruoslahti et al. | |

FOREIGN PATENT DOCUMENTS

| | | |
|---|---|---|
| EP | 1773416 B1 | 12/2010 |
| WO | 2006/003442 A2 | 1/2006 |

OTHER PUBLICATIONS

Pernot et al Real-Time Assessment of Myocardial Contractility Using Shear Wave Imaging, Journal of the American Colege of Cardiology, col. 58, No. 1, 2011, pp. 65-72.*
Pernot et al (Real-Time Assessment of Myocardial Contractility Using Shear Wave Imaging, Journal of American College of Cardiology, col. 58, No. 1, 2011).*
Pernot et al (Real-Time Assessment of Myocardial Contractility Using Shear Wave Imaging, Journal of American College of Cardiology, col. 58, No. 1, 2011 (Year: 2011).*
Jasiuk, et al., "Modeling of bone at a single lamella level," Biomechan Model Mechanobiol (2004) 3: 67-74.
Ouchi, et al., "Follistatin-like 1, a secreted muscle protein, promotes endothelial cell function and revascularization in ischemic tissue through a nitric-oxide synthase-dependent mechanism," The Journal of Biological Chemistry, vol. 283, No. 47, pp. 32802-32811.
Shimano, et al., "Cardiac myocyte follistatin-like 1 functions to attenuate hypertrophy following pressure overload," PNAS, Oct. 25, 2011, vol. 108, No. 43, E899-E906.
Alekseeva, et al., "Engineering stable topography in dense biomimetic 3d collagen scaffolds," European Cells and Materials, vol. 23, 2012, pp. 28-40.
Gaballa, et al., "Grafting an acellular 3-dimensional collagen scaffold onto a non-transmural infarcted myocardium induces neoangiogenesis and reduces cardiac remodeling", The Journal of Heart and Lung Transplantation, vol. 25, No. 8, Aug. 2006, pp. 946-954.
Gojo, et al., "Cardiac regenerative medicine, cellular therapy and tissue engineering," Circulation Journal, 2009; Supplement A; A-61-A-67.

(Continued)

*Primary Examiner* — Micah Paul Young
(74) *Attorney, Agent, or Firm* — Brian E. Davy; Bozicevic, Field & Francis LLP

(57) ABSTRACT

Disclosed is a patch system for use in a patient with a damaged heart. The patch comprises both a biodegradable engineered collagen scaffold to provide structural support to the injured heart and therapeutic agents, which are delivered by the patch to the heart. The scaffold consists of a dense collagen lamella produced by plastic compression with biomechanical properties that make it compatible with beating heart tissue, e.g. stiffness in a predefined range. One therapeutic agent, Fstl1, is shown to induce cardiomyocyte proliferation and enhance cardiac regeneration after injury. The patch can also be loaded with functionalized nanoparticles to yield multi-modal imaging capabilities in vivo. Also disclosed is a method for implanting the patch onto a patient's heart.

16 Claims, 18 Drawing Sheets

Specification includes a Sequence Listing.

(56) References Cited

Mahdy, et al., "Antimicrobial activity of zero-valent iron nanoparticles", International Journal of Modern Engineering Research, vol. 2, Issue 1, Jan.-Feb. 2012, pp. 578-581.

Hajipour, et al., "Antibacterial properties of nanoparticles", Trends in Biotechnology, doi: 10.1016/j.tibtech.2012.06.004, 2012, 13 pages.

Zammaretti, et al., "Cardiac tissue engineering: regeneration of the wounded heart:", Current Opinion in Biotechnology 2004, 15:430-434.

Mercola, et al. "Cardiac muscle regeneration: lessons from development", Genes & Development, 25:299-309 2011.

Hadjipanayi, Ektoras, "Engineering physical structure in biomimetic collagen scaffolds: strategies for regulating cell behavior", PhD Thesis, Jul. 2010, Institute of Orthopaedics and Musculoskeletal Science, University College London, Royal National Orthopaedic Hospital, Brockley Hill, Stanmore, Middlesex, HA7 4LP.

\* cited by examiner

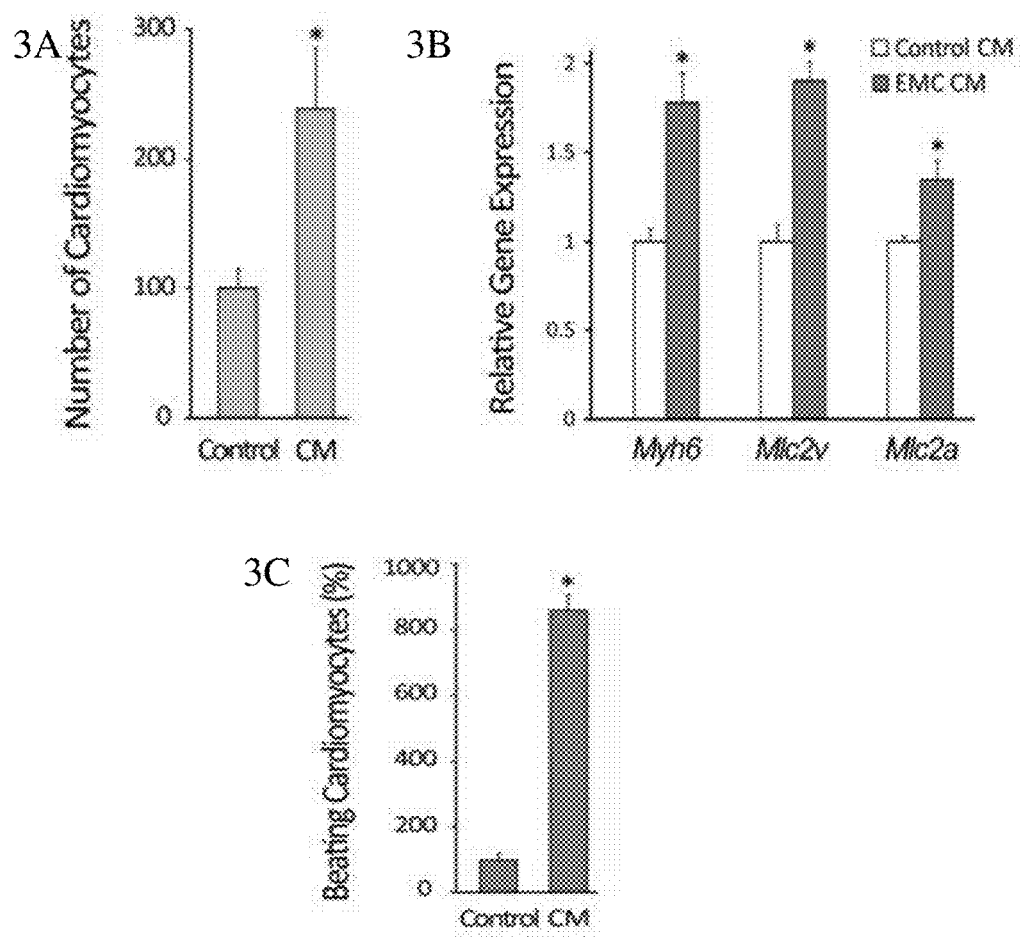
Figure 3A, B, C

ENGINEERED COLLAGEN MATRICES FOR MYOCARDIAL THERAPY

CROSS-REFERENCE TO RELATED APPLICATIONS

This application claims priority from U.S. Provisional Patent Application No. 61/718,046, filed Oct. 24, 2012, and U.S. patent application Ser. No. 14/062,385, filed Oct. 24, 2013, which are hereby incorporated by reference in their entirety.

STATEMENT OF GOVERNMENTAL SUPPORT

This invention was made with Government support under contracts HL65484 and HL86879 awarded by the National Institutes of Health. The Government has certain rights in this invention.

REFERENCE TO SEQUENCE LISTING, COMPUTER PROGRAM, OR COMPACT DISK

The instant application contains a Sequence Listing which has been submitted as an ASCII text file and is hereby incorporated by reference in its entirety. This text file was created on 10/23/2013 is named "3815_109_1_Seq_List.txt" and is 4,476 bytes in size.

BACKGROUND OF THE INVENTION

Field of the Invention

The present invention relates to the field of repairing and regenerating heart tissue, and, more specifically, to materials and methods using therapeutic agents such as peptides, proteins or small compounds seeded within engineered collagen matrices.

Related Art

Presented below is background information on certain aspects of the present invention as they may relate to technical features referred to in the detailed description, but not necessarily described in detail. The discussion below should not be construed as an admission as to the relevance of the information to the claimed invention or the prior art effect of the material described.

Due to the limited self-renewal capacity of cardiomyocytes, the mammalian heart exhibits impaired regeneration and insufficient ability to restore heart function after injury. Over the past 80 years, heart diseases have been the leading cause of death and morbidity in the US, with substantial health care expenditures. As reported by the American Heart Association, by 2030, 40 percent of US adults, upwards of 116 million people, will be suffering from cardiovascular diseases. Cardiovascular-related disease costs will triple between 2010 and 2030 to more than $800 billion a year. Among these diseases, heart stroke holds the highest rate of mortality, accounted for 1 of every 18 deaths in the US in 2007. Patients who survive acute myocardial infarction (MI) are left with damaged ventricles, prone to scar formation and aneurismal thinning, which often lead to heart failure.

Current clinical therapies for severe heart injuries, primarily focused on cell transplantation, have shown modest success at best. This is due to factors including poor penetration, low cardiac engraftment efficiency, deficient viability and retaining of the cells at the site of injury, and the lack of control on the fate of the grafted cells. Therefore, a dire need exists for the development of alternative cardiac regenerative approaches.

Grafting of tissue engineering scaffolds onto the injured cardiac tissue has been recently introduced as an alternative therapy to influence cardiac regeneration and remodeling processes post ischemia. A few attempts have been made to produce commercially available cardiac patches, mainly by utilizing naturally-occurring matrices (decellularized tissues). However, the cardiac patch success has been limited primarily due to the poor control on the ultrastructure and physiomechanical properties of the matrix and therefore, mismatch of the patch-host tissue properties, inflammatory response, insufficient vascularization and thrombosis, and lack of appropriate macromolecules within the patch in order to effectively intervene with post-injury processes.

As the most common extracellular matrix (ECM) protein in the human body, type I collagen has been extensively used to produce scaffolds for tissue regeneration purposes. Recently developed plastic compression (PC) technique can be applied to hydrated collagen gels in order to produce dense scaffolds with precisely tuned properties such as stiffness, pore size, density, and fibril orientation. Prior to polymerization, various factors including cells and therapeutic macromolecules can be added to the liquid collagen solution, resulting in a uniform distribution of the factors within the 3D scaffold structure post gelation. Accordingly, compressed collagen matrices, mimicking native cardiac tissue-structure and properties, and seeded with recently identified cardiogenic factors, can be utilized as promising alternatives to treat acute ischemic heart injuries.

Repairing cardiac tissue after injury is a long sought yet proven difficult task. It requires understanding of cardiac injury and repair at molecular, cellular and tissue level to design proper treatments. In order to achieve maximum effect, the right combination of treatments on different levels and in a coordinated way has to be established. Cardiac patches, used as engineered devices to deliver cells to the heart, are promising tools in treating injured heart. However, the safety limitation of cell therapy encourages the usage of acellular patches containing therapeutic agents. It has been proposed that paracrine factors secreted by epicardium are important for the growth of myocardium. Recent studies showed that epicardium-derived factors increase coronary angiogenesis after injury, further suggesting a regenerative potential of epicardial signaling. Combining epicardial inductive signaling with tissue engineering paradigm could provide a novel, safe and powerful alternative approach to treat cardiac injury. However, whether epicardial paracrine signaling can activate regeneration in the adult mammalian heart, let alone the identity of such epicardial factors, remains elusive.

SPECIFIC PATENTS AND PUBLICATIONS

Serpooshan, et al., "The Effect of Bioengineered Acellular Collagen Patch on Cardiac Remodeling and Ventricular Function post Myocardial Infarction", Biomaterials 34, 9048, (2013), describes for the first time the application of the engineered acellular collagen patch, introduced in this patent, grafted onto infarcted myocardium of the left ventricle in male mice, on cardiac function and heart tissue structure. In comparison to infarcted hearts with no treatment, hearts bearing patches preserved contractility and significantly protected the cardiac tissue from injury at the anatomical and functional levels. This improvement was accompanied by attenuated left ventricular remodeling, diminished fibrosis, and formation of a network of interconnected blood vessels within the infarct. Histological and immunostaining confirmed integration of the patch with native cardiac cells including fibroblasts, smooth muscle cells, epicardial cells, and immature cardiomyocytes. In summary, an acellular biomaterial with specific biomechanical properties promotes the endogenous capacity of the infarcted myocardium to attenuate remodeling and improve heart function following myocardial infarction.

Gaballa, et al., "Grafting An Acellular 3-Dimensional Collagen Scaffold Onto a Non-transmural Infarcted Myocardium Induces Neo-angiogenesis and Reduces Cardiac Remolding," J. Heart and Lung Transpl. 25(8): 946-954 (2006), describes an acellular collagen type 1 scaffold grafted onto infarcted myocardium of the left ventricle in rats. No physiomechanical assessment was conducted. Furthermore, no cardiogenic factors were added to the patch. Although, patch integration and increased vessel density were observed 6 weeks post implantation, there was no evidence on cardiac function improvement or cardiac muscle regeneration.

United States Patent Publication 2008/0131473 by Brown et al., "Cell-Independent Fabrication of Tissue Equivalents," discloses a tissue equivalent implant comprising collagen fibers and interstitial fluid wherein the interstitial liquid comprises viable cells, including stem cells. Also, the scaffold is not disclosed as having physiomechanical properties or additives appropriate for use in myocardial infarction therapy.

United States Patent Publication 2010/0196441 by Sondermeijer et al., "Uses of Immunologically Modified Scaffold for Tissue Prevascularization Cell Transplantation," discloses an alginate scaffold that comprises the RGD peptide and may be used for cardiac repair. The Sondermeijer et al. patch was not shown to regenerate epicardium or myocardium tissue. Moreover, the approach in Sondermeijer et al. does not offer the possibility of adjusting or tailoring the patch properties. In contrast, by changing the plastic compression properties to the current patch, patches with significantly different stiffness, porosity, etc. can be produced.

Zamaretti et al., "Cardiac tissue engineering: regeneration of the wounded heart," Current Op. Biotech. 15:430-434 (2004), revises previous work using collagen for cardiac tissue engineering.

Alekseeva et al., "Engineering Stable Topography in Dense Bio-mimetic 3D collagen Scaffolds," Eur. Cell. and Materials 23:28-40 (2012), discloses current work in compressed collagen gels for organizing cell growth. Properties of a collagen scaffold required for cardiac repair are not discussed.

Brown et al. WO/2006/003442, "Cell-independent fabrication of tissue equivalents," published Jan. 12, 2006, describes processes which mimic cellular bioremodelling and produce organized biomaterials which have mechanical properties and viable cell densities suitable for use as functional tissue implants. No particular parameters of myocardio-compatible scaffolds are given, such as an appropriate stiffness.

Serpooshan et al., "Reduced hydraulic permeability of three-dimensional collagen scaffolds attenuates gel contraction and promotes the growth and differentiation of mesenchymal stem cells," Acta Biomaterialia 6:3798-3987 (6 May 2010) discloses plastic compression to rapidly generate tissue scaffolds with controlled collagen fibrillar densities (CFDs) approaching those of native tissues. Plastic compression significantly improves the biomechanical properties of collagen scaffolds without adverse effects on the viability and metabolism of resident cells. Control of permeability (k) influenced the effect of induced microstructural changes on MSC (mesenchymal)-induced gel contraction. Mechanical properties such as stiffness, or applications of any plastic-compressed scaffolds to cardiac tissue are not discussed.

BRIEF SUMMARY OF THE INVENTION

The following brief summary is not intended to include all features and aspects of the present invention, nor does it imply that the invention must include all features and aspects discussed in this summary.

The present invention comprises a biodegradable scaffold with pre-defined physiological and mechanical properties which make it effective after implantation onto epicardium or myocardium tissue. The biodegradable scaffold comprises compressed collagen having properties consistent with those of healthy myocardium and further comprises a therapeutic composition on or within the scaffold for promoting regeneration of heart tissue. Key physical properties are stiffness and contractility, whereby the scaffold can move with beating heart tissue.

In certain aspects, the present invention comprises a scaffold for implantation into myocardium, comprising: (a) a cell-free collagenous material consisting of a layer of thin dense lamella and (ii) a stiffness approaching that of embryonic epicardium, consistent with contractility of normal myocardium, ranging from 1 to 10 kPa; and (b) a composition, in the scaffold, comprising a factor secreted by epicardial cells, the composition being present in an amount sufficient to promote regeneration of heart tissue. The scaffold uses cell-free of endogenous cells from collagen, but the final patch may comprise cardiac type cells.

The scaffold can also be included into a meshed material to provide attachment to the heart and minimize scarring.

The scaffold is referred to as a "3D," or three dimensional composite or scaffold, that it has a thickness as well as length and width, giving it certain mechanical properties, such as stiffness, compressability (or non-compressability), pore size, hydration capacity, etc. These materials can be made in clinically relevant sizes, e.g. 0.5-50 $cm^2$. The therapeutic composition or agent can be, e.g. conditioned media, certain peptides, or cells.

In certain embodiments, the therapeutic composition within the scaffold may comprise epicardial-conditioned media and/or factors contained in such conditioned media, such as those secreted by epicardium-derived cells. Such factors are termed paracrine factors. Such peptidic factors include follistatin-like1 (Fstl1) protein, which has been found to be especially effective in regenerating myocardial tissue. Other paracrine factors secreted by EMCs may be used, e.g. protein products of genes such as Igfbp2 (Insulin-like growth factor-binding protein 2), Prss 1(Anionic trypsin-1), Clu (Clusterin), Ogn (osteoglycin), Timp2 (Metalloproteinase inhibitor 2), Pxdn (peroxidasin), Sparc (SPARC, osteonectin), C1r (complement C1r subcomponent), Igfbp7 (Insulin-like growth factor binding protein 7), Olfml3 (olfactomedin-like 3), Metrnl (Meteorin-like protein), Serpinf1 (Serine (Or cysteine) peptidase inhibitor, clade F, member 1), Bmp1 (bone morphogenetic protein 1), Pdgfa (Platelet-derived growth factor subunit A), and Crip2 (Cysteine-rich protein 2).

The therapeutic composition within the scaffold may also comprise cardiomyocytes or cardiomyocyte precursors.

For monitoring and observation, in some aspects these cells may be fluorescently labeled.

The present invention also contemplates that the therapeutic factors may be mixed while the collagen is in a fluid state, and then embedded into the 3D matrix. In certain aspects, the present invention comprises methods for implanting the patch as described herein into a patient in order to promote the healing of heart tissue. Such a method comprises the steps of (1) adding an effective amount of a therapeutic composition to the pre-polymerized scaffold, (2) preparing a compressed collagen scaffold having predetermined physiomechanical properties consistent with those of healthy myocardium or epicardium, and (3) implanting the scaffold onto the heart of a patient, thereby inducing healing/regeneration of heart tissue.

The present device can be also used as a 3D in vitro model to study the biologic phenomena involved in the heart development and repair, by providing a biomimetic microenvironment to the cells. This model would be best applicable to several in vitro studies of cardiovascular cell biology including cell signaling, migration, proliferation, and differentiation assays.

BRIEF DESCRIPTION OF THE DRAWINGS

FIG. 2A is a bar graph showing the quantification of the number of cardiomyocytes with or without co-culturing with EMCs (epicardial/mesothelial cells). FIG. 2B is a bar graph showing Myh6 gene expression increased in mCM-d2 upon co-culturing with EMCs, normalized to GAPDH gene expression FIGS. 3A, 3B, and 3C is a set of graphs showing the effect of epicardial conditioned media on cardiogenesis. FIG. 3A shows the quantification of the number of cardiomyocytes with or without epicardial conditioned media. FIG. 3B shows the expression of cardiac-specific markers in mCM-d2 after 8 days of treatment in epicardial conditioned media, normalized to GAPDH expression. FIG. 3C shows the quantification of the number of cardiomyocytes with rhythmic calcium transient in control and in epicardial conditioned media using KIC instrument. * statistically different from control ($P<0.05$).

FIG. 5A is a 2 μm-flat AFM tip. FIG. 5B is a histogram that demonstrates the distribution of measured microstiffness of the patch. These values are also compared with optimal range of stiffness to attain maximum cardiomyocyte work (contractility).

FIG. 9A shows the quantification of numbers of cardiomyocytes with or without fstl1 treatment. FIG. 9B shows the expression of cardiac-specific markers in mCM-d2 after 8 days of treatment in Fstl1, normalized to GAPDH expression. FIG. 9C shows the quantification of cardiomyocytes with rhythmic calcium transient with or without fstl1 treatment using KIC instrument.

FIG. 12A shows representative trichrome staining of hearts in Sham, MI-only, MI+Patch and MI+Patch+Fstl1 groups, 4 weeks post surgery. LV remodeling post infarction was significantly inhibited after patch implantation, with remarkably limited fibrosis and diminished LV wall thinning. FIG. 12B shows the quantification of the percentage of fibrotic area.

FIG. 17 A shows a number of α-actinin positive cells per plate in mCM-d2 cultures with or without FSTL1 treatment (n=8). FIG. 17 B shows expression of cardiac-specific markers in mCM-d2 after 8 days of treatment in FSTL1, normalized to Gapdh expression (n=3). FIG. 17C shows a number of cardiomyocytes/plate with rhythmic calcium transients. Contractile Ca2+ transients recorded automatically (n=6 biological replicate samples, each >200 cardiomyocytes) * ($p<0.05$)

FIGS. 17A, 17B, and 17C is series of photographs showing MRI analysis of pig I/R after 14 days of patch FSTL1 implantation.

DETAILED DESCRIPTION OF THE PREFERRED EMBODIMENT

Overview

Figure 1A:
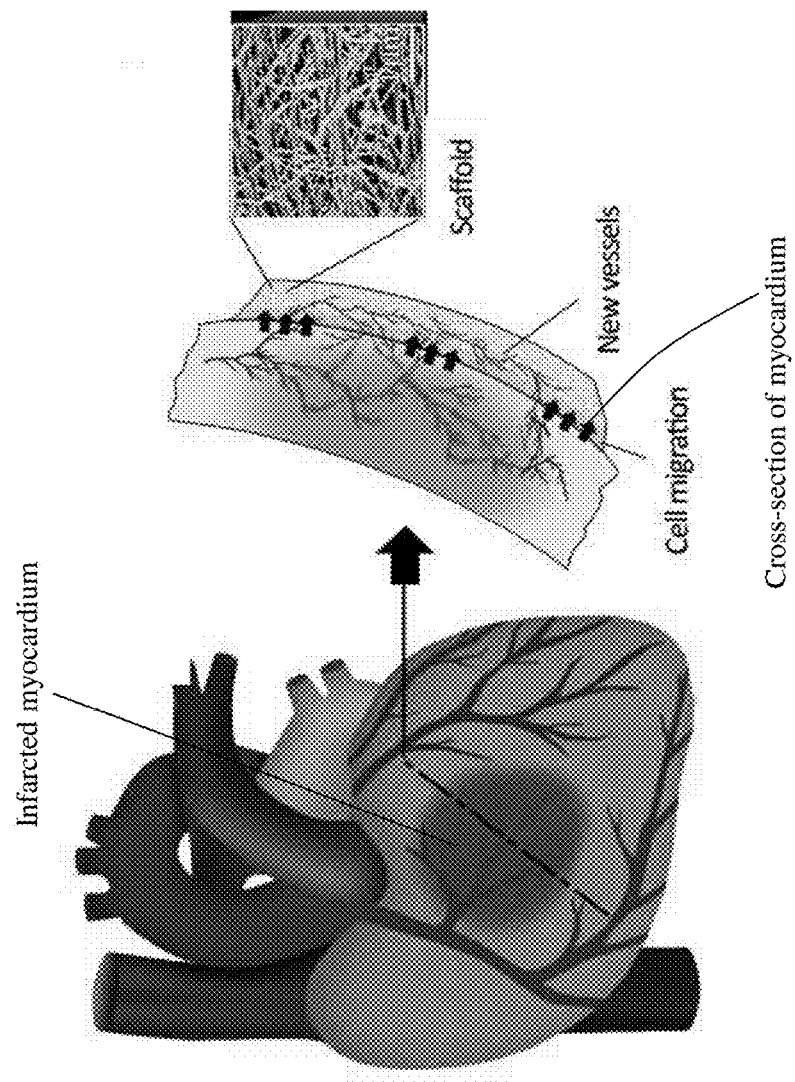
FIG. 1A shows a schematic representation showing the dense collagen patch and plastic compression levels, respectively. The drawing shows that an infracted myocardium and a blown up view of the infarcted myocardium illustrating the scaffold attached to an area of the infarction, and cells and new vessels infiltrated into the scaffold.

Described herein are novel cardiovascular patches designed to be applied to damaged cardiac tissue and to promote healing of the damaged tissue. The patches comprise a biodegradable collagen material in the form of a scaffold that is engineered physio-mechanically by a compression process, preferably plastic compression. The scaffold is preferably loaded with therapeutic factors to promote cardiac regeneration and implanted onto a contactile tissue that has been damaged, preferably at or near a site of infarction. The thus-formed patch will serve to protect the cardiac tissue from further injury both at the anatomical and functional levels. Thus, the epicardial patch is designed with plastic compressed (PC) collagen scaffolds having predetermined physiomechanical properties consistent with those of healthy myocardium.

Collagen Material

As noted above, the plastic compression (PC) technique allows for the production of dense scaffolds (i.e. having a dense, packed layer and a more porous layer within the unitary collagen material) with precisely tuned properties such as stiffness, pore size, density, and fibril orientation. This also allows for a collagen scaffold having a first layer of hydrated collagen attached to a second layer of compressed collagen having dense fibrillar nanostructure.

The collagen material may be prepared from in vitro reconstituted type 1 collagen gels, as exemplified below. The collagen is first prepared as a highly hydrated gel, then compressed as described below. Reconstituted type 1 collagen may be prepared, for example, from tissue (e.g. corium) that has been limed, fragmented, swollen in acid, precipitated, washed with distilled water and isopropanol, as described e.g. in Silver, et al. U.S. Pat. No. 5,171,273, entitled "Synthetic collagen orthopaedic structures such as grafts, tendons and other structures," issued Dec. 15, 1992. Collagen material for use in the present patches may also be recombinant, as described e.g. in Kivirikko et al. US 2005/0164345, entitled "Synthesis of human procollagens and collagens in recombinant DNA systems," published Jul. 28, 2005. The collagens produced by these methods, hosts, and vectors include both homotrimer and heterotrimer collagen.

The present collagen material can be rat tail-extracted collagen, bovine collagen, human collagen or a recombinant single type of collagen, such as and human type I collagen. Alternatively, other cartilaginous materials such as proteoglycans or elastin can be used. For example, U.S. Pat. No. 6,306,169 (Lee) discloses an implant consisting of a porous macrostructure the pores of which are filled up with a hydrated gel. The macrostructure is made of a bioresorbable polymer (collagen, gelatin, poly-L-lactic acid, polycaprolactone, polyhydroxybutarate, or polyanhydrides) and the non-porous, hydrated gel consists of alginate, agarose, carrageenans, glycosaminoglycans, proteoglycans, polyethyelene oxide or collagen monomers.

The present collagen material is not cross-linked. Cross-linking has the potential to deteriorate the biocompatibility of the patch due to various levels of cytotoxicity found in cross-linking agents. In addition, cross-linking may also cause a change in the physiomechanical properties of the patch, such as stiffening, which would result in the patch no longer being able to mimic healthy cardiac tissue.

Preparation and Properties of the Collagen Material

Described in detail below is a method by which a collagen scaffold may be prepared so as to be compatible with contractile tissue. The present scaffold should be porous in 3D in order to contain a therapeutic composition (the combination referred to here as a "patch") and to allow infiltration by growing cells around the patch; it should have the requisite stiffness and flexibility to remain in place on contracting and expanding tissue; it should be hypoallergenic and bioabsorbable; and it should not shrink after implantation.

It has now been found that plastic compression of a collagen gel can produce stiffness values between 0-1 and 25 kPa, or about 0-1-10 kPa, which can result in effective patches when implanted into suitable animal models. As is known in the art, Pa ($N/m^2$ or $m^{-1} \cdot kg \cdot s^{-2}$), is a Pascal, a unit of measurement of a change in the dimension of a bar made of an isotropic elastic material under tensile or compressive loads. This stiffness is measured along the thickness of the patch, as described in detail below.

As described below, the preferred properties were obtained using a plastic compression apparatus where a circular patch with a diameter of ~16 mm and thickness of ~200 μm was made via application of a pressure of 1400 Pa for 5 minutes. Patches may be sized as desired, and pressures may be applied from about 300 Pa to 1400 Pa for 2 minutes to 5 minutes.

Therapeutic Compositions

A unique advantage of the present epicardial patch is that it also contains a therapeutic composition on or in the scaffold for promoting regeneration of heart tissue and neovessels with the scaffold. The therapeutic composition preferably comprises factors such as found in conditioned media from epicardial-like cultures. These media contain an activity that enhances cardiogenesis in embryonic-derived stem cells. Before now, the nature of the factors and whether they can be used as therapeutic agents for tissue regeneration and repair in an injured heart were largely unknown.

While the therapeutic agent may be selected from conditioned media, bioactive drugs, peptides, or cells, recent evidence suggests that the epicardium promotes myocardial development and regeneration, potentially by secretion of paracrine factors. Mass-spectrometry and subsequent analyses, described in the examples herein, revealed that follistatin-like 1 is a main component of the cardiogenic activity of the epicardial-conditioned media.

Scaffold matrices loaded with follistatin-like 1 recapitulated the effect of the epicardial patch and almost completely reverted the infarct size, contractility, and end- diastolic and systolic cardiac function of infarcted mice. A significant amount of viable connective tissue, proliferating cardiomyocytes, and a network of interconnected blood vessels that were specifically induced by the engineered tissue accompanied the restored cardiac function. Immuno-histochemistry confirmed the existence of mature as well as immature proliferating cardiomyocytes, fibroblasts, smooth muscle, and epicardial cells within the grafted area.

In order to prepare a patch using one or more protein factors such as listed above, one may either obtain the desired protein(s) in purified form commercially, or prepare them by known recombinant DNA technology. For example, human fstl1 is obtainable from Adipo Bioscience, Inc. Santa Clara Calif. One may use the gene designations provided herein to obtain the DNA sequence from GenBank, or the amino acid sequence from UniProt and design appropriate expression vectors. The expressed peptide may then be purified by known methods.

Therapeutic compositions useful in the present invention may further comprise a nucleic acid encoding the desired factor. The nucleic acid may be contained in an mRNA or DNA construct. Such constructs are known for so-called "naked DNA" gene therapy. See, e.g. Debs et al. U.S. Pat. No. 6,627,615, "Methods and compositions for in vivo gene therapy," for further guidance on the use of such compositions, e.g. with lipid carriers.

In other embodiments, the therapeutic composition comprises cells, such as embryonic or adult stem cells. Details on preparing cardiomyocyte stem cells may be found e.g. in Xu US 2003/0022367, "Cardiomyocyte precursors from human embryonic stem cells." Along these lines, one may also apply to the scaffold a stem cell chemotractant peptide, or a stem-cell stimulating peptide such as G-CSF, hepatocyte growth factor (HGF), Stromal cell derived factor 1 (SDF-1). Another potential therapeutic protein is perostin. Periostin expression is minimal in adult hearts but is upregulated after injuries including MI where it plays a role in remodeling of the extracellular matrix. Another protein that recently has gained interest as a possible mitogen for myocytes is neuregulin. See, Segers et al., "Protein Therapeutics for Cardiac Regeneration after Myocardial Infarction," J Cardiovasc Transl Res. 3: 469-477 (July 2010).

In an alternative embodiment, the therapeutic composition may be administered after the scaffold is placed onto the myocardium.

Other factors may be used in the present therapeutic compositions, such as Vegfa, Angpt1, Ang, Fgf1, Fgf2, Fgf9, Pdgfa, Pdgfc, Pdgfd, Adamts1, Sdf1, Mcp1, GDF15 and I16.

The therapeutic composition may also comprise cardiomyoctes or cardiomyocyte precursors. These may be human cells for implantation into a human subject. These may be induced pluripotent stem cells. One may obtain, for example, from Axiogenesis AG, Cologne Germany, cardiomyocytes designated Cor.4U. The cells have been generated from an iPS line with a Caucasian background. The dedifferentiation was carried out according to the protocols described by Yamanaka et al. Cell lines may be obtained with a GFP reporter transgene.

Methods of Treatment

Also described herein are methods and procedures for promoting the regeneration of heart tissue by implantation of the patch into a patient. The method comprises:

(1) adding a therapeutic composition to the scaffold material in an amount effective to stimulate myocardial repair;
(2) preparing a compressed collagen scaffold of claim 1 having predetermined physiomechanical properties consistent with those of healthy myocardium; and
(3) implanting the scaffold onto the heart of a patient by applying the scaffold to an outer surface of an infracted area of the patient's heart.

The implantation of the present patch may be accomplished by surgically opening the chest of a patient and retracting the lungs to expose the heart or by small incision in the thoracic cavity. The infracted area of the myocardium is then identified and the scaffold is grafted onto the damaged tissue. Alternatively, the patch may be implanted interventionally rather than surgically opening the chest. The patch is preferably applied directly to the myocardium. This can be done by applying the patch to the infracted area of the heart, where the outermost layer of epicardial cells is no longer present.

In a preferred embodiment, the present patch is applied to an area of infarcted myocardium by means of endoscopic surgery. In one embodiment, the patch is applied as an envelope surrounding all or a substantial portion of the heart.

Follistatin-Related Protein 1 (FSTL1)

The present materials and methods provide novel strategies to enhance the limited endogenous regenerative potential of the injured heart. Paracrine factors from the epicardium might naturally enhance myocardial regeneration, and therefore might be adapted therapeutically. Follistatin-related protein 1 (FSTL1) has been identified as promoter of regeneration of epicardium.

FSTL1 (aka FRP, Flik, and TSC-36) is a secreted glycoprotein belonging to the BM-40/SPARC/Osteonectin family that shares a single cysteine-rich domain with Follistatin, an Activin-inhibiting protein. FSTL1 also contains an extracellular calcium-binding domain plus a region with homology to the von Willebrand Factor type C domain. Unlike its namesake, FSTL1 does not block activin. Its biochemical function is poorly characterized, although it can inhibit BMP possibly by direct interaction. Loss of BMP inhibition might underlie some of the lung and skeletal defects of the FSTL1 KO mice, which die at birth most likely because of the lung defects. Independently of BMP inhibition, FSTL1 might signal in its own right, for instance to activate Akt in muscle cells, increasing eNOS phosphorylation and capillary density in ischemic hind limbs. The cell surface receptor responsible for transducing a FSTL1 signal is not well characterized, although a Biocore study revealed binding to disco-interacting protein 2 homolog A (DIP2A), CD14 and glypican1 (See Tanaka M, Murakami K, Ozaki S, Imura Y, Tong X P, Watanabe T, et al. DIP2 disco-interacting protein 2 homolog A (*Drosophila*) is a candidate receptor for follistatin-related protein/follistatin-like 1-analysis of their binding with TGF-beta superfamily proteins. FEBS J. 2010; 277(20):4278-89.)

Despite major recent progress on the mechanisms of cardiac regeneration and survival to stress, much is left to know before the establishment of comprehensive model of crosstalk between these two parallel mechanisms and to advance new pro-survival and regenerative therapies that address the growing problem of heart failure. In this regard, FSTL1 is a secreted factor that has been proposed as cardioprotective via AKT and AMPK activities. (See Shimano M, Ouchi N, Nakamura K, van Wijk B, Ohashi K, Asaumi Y, et al. Cardiac myocyte follistatin-like 1 functions to attenuate hypertrophy following pressure overload. Proc Natl Acad Sci USA. 2011; 108(43).)

A second and unexpected function for FSTL1 as an activator of myocyte expansion after injury is described here. As described below, FSTL1 is expressed in the epicardium in the un-injured heart, but this epicardial expression is completely obliterated after myocardial infarction (MI). Strikingly, however, cardiac regeneration is observed after epicardial delivery of FSTL1, suggesting that the loss of expression precludes a potentially beneficial effect. It has been observed here that in vitro and in vivo treatments with recombinant FSTL1 induce the proliferation of precursor myocytes. These data corroborate the notion of the epicardium as a supportive tissue for myocardial regeneration, notably for the first time attributing an effect to an epicardial-derived protein. Without being bound by the present scientific theory, our mechanistic working hypothesis is that FSTL1 supports a sub-epicardial niche that allows the expansion of target, progenitor/precursor cells.

Definitions

Unless defined otherwise, all technical and scientific terms used herein have the same meaning as commonly understood by those of ordinary skill in the art to which this invention belongs. Although methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

Ranges: For conciseness, any range set forth is intended to include any sub-range within the stated range, unless otherwise stated. As a non-limiting example, a range of 2-25 is intended to include a range of about 12-20, 10-13, 2-22, 3-15, etc. The term "about" has its ordinary meaning of approximately and may be determined in context by experimental variability. In case of doubt, "about" may be taken to means plus or minus 5% of a stated numerical value.

The term "collagen" as used herein refers to is a group of naturally occurring proteins found in animals, especially in the flesh and connective tissues of vertebrates. Collagen is a composed of a triple helix, which generally consists of two identical chains (al) and an additional chain that differs slightly in its chemical composition (α2). The tropocollagen or collagen molecule is a subunit of larger collagen aggregates such as fibrils.

The term "collagenous material" as used herein refers to collagen as defined above. It may include, unless otherwise specified, bovine collagen, porcine collagen, human collagen (i.e. human-sourced) and human type I collagen, recombinant. It may also include mixtures of various collagen types or single types, such as type I, II, IV, V, etc., as long as a solid article is formed. Other collagenous materials, unless a collagen material is specified, include collagen-like peptides, alginate, etc. as described herein. The term "cell-free collagenous material" means that the collagen as obtained from animals has been depleted of those animals associated with the collagen protein, or that it is synthesized and separated from any cells used.

As used herein the term "collagen fibril" refers to a quasi-crystalline, filamentous structure or single lamella formed by the self-assembly of soluble collagen molecules. The engineered matrices comprise collagen fibrils which may pack in a quarter-staggered pattern giving the fibril a characteristic striated appearance or banding pattern along its axis. Collagen fibrils are distinct from the amorphous aggregates or precipitates of insoluble collagen that can be formed by dehydrating (e.g., lyophilizing) collagen suspensions to form porous network scaffolds.

The terms "peptide," "polypeptide" and "protein" are used interchangeably herein to refer to an amino acid chain with two or more amino acid residues, and also includes branched and circularized amino acid chains.

The term "epicardium" as used herein refers to the outer layer of tissue surrounding the heart and is in contact with the myocardium.

The term "myocardium" as used herein refers to the middle layer of tissue within the walls of the heart. The myocardium is composed of muscular heart tissue, responsible for contracting to push blood out of the heart.

The term "epicardial cell conditioned media" as used herein refers to cell culture media that has been used to culture epicardium-derived cells. Thus there is produced media containing biologically active components obtained from the previously cultured epicardial cells, which have released into the media substances affecting certain cell functions (e.g., growth, lysis).

The term "dense lamella" as used herein refers to the dense layer of collagen which forms as a result of plastic compression, at the fluid expulsion surface. This layer has hydraulic permeability which is at least about 100 fold less than a non-compressed, hydrated collagen. Hydraulic permeability may be measured as described in Serpooshan et al., "Characterization and modelling of a dense lamella formed during self-compression of fibrillar collagen gels: implications for biomimetic scaffolds," Soft Matter 6:2918-2926 (2 Feb. 2011). As described there, Under free fluid flow conditions, highly hydrated fibrillar collagen gels expel fluid and undergo a gravity driven consolidation process (self-compression). Within minutes of the initiation of self-compression, collagen scaffolds with fibrillar densities resembling those of native tissues are produced. The dense lamella form a thin dense lamella after compression, i.e. on the order of 50-300 μm in thickness, or sub-ranges, e.g. 100-300, 150-250, etc. As understood in the art, collagen lamella are a spatially random of network of collagen fibrils.

The term "Fst1-1" "FSTL-1", or "follastatin-like 1", as used herein, refers to a protein encoded by the FSTL1 gene and that has similarity to follistatin, an activin-binding protein. It contains an FS module, a follistatin-like sequence containing 10 conserved cysteine residues. This gene product is thought to be an autoantigen associated with rheumatoid arthritis. Fstl1 encodes a deduced 308-amino acid protein (below) with an N-terminal signal peptide of 20 amino acids. The number and distribution of the cysteine residues supports the existence of several intramolecular disulfide bridges. Immunohistochemical analysis demonstrated increased expression in Cd90 (THY1)-positive fibroblasts, particularly early in CIA. Monkey fibroblasts transfected with human FSTL1 spontaneously secreted more IL6, and human monocytes transfected with FSTL1 and stimulated with mitogens expressed higher IL1B, TNF, and IL6.

In particular, fstl-1 refers to the human protein having the sequence of SEQ ID NO: 1:

```
          10         20         30         40         50         60
    MWKRWLALAL ALVAVAWVRA EEELRSKSKI CANVFCGAGR ECAVTEKGEP TCLCIEQCKP 70         80         90        100        110        120
    HKRPVCGSNG KTYLNHCELH RDACLTGSKI QVDYDGHCKE KKSVSPSASP VVCYQSNRDE 130        140        150        160        170        180
    LRRRIIQWLE AEIIPDGWFS KGSNYSEILD KYFKNFDNGD SRLDSSEFLK FVEQNETAIN 190        200        210        220        230        240
    ITTYPDQENN KLLRGLCVDA LIELSDENAD WKLSFQEFLK CLNPSFNPPE KKCALEDETY
```

-continued

```
         250         260         270         280         290         300
ADGAETEVDC NRCVCACGNW VCTAMTCDGK NQKGAQTQTE EEMTRYVQEL QKHQETAEKT
KRVSTKEI
``` as given in UniProt entry Q12841.

The term fstl-1 also includes the mature form of the protein (aa 21-308) and known human polymorphisms.

The term "fstl-1" peptide" is intended to be somewhat more general than the term fstl-1 and includes sequence variations and active fragments of fstl-1 as set forth in the sequence above.

Figure 1B:
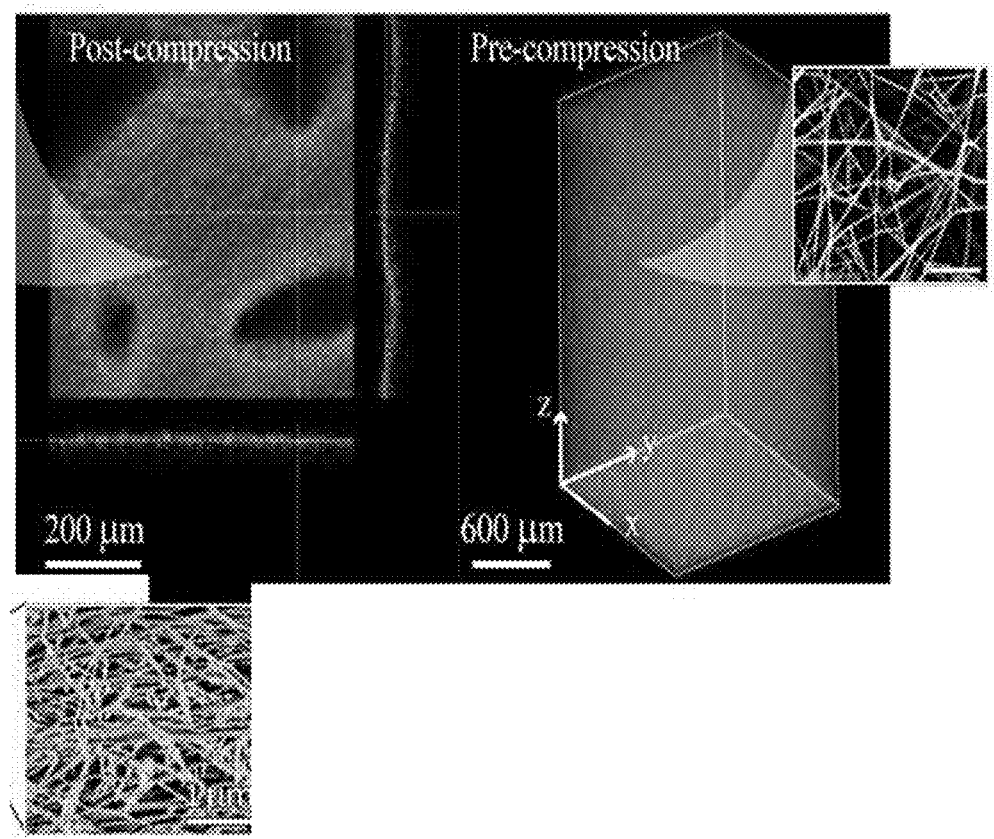
FIG. 1B is a photograph that shows prior art confocal microscopy images of collagen scaffolds and pre- (right) and post- (left) plastic compression process, adapted from Serpooshan et al. Characterization and modelling of a dense lamella formed during self compression of fibrillar collagen gels: implications for biomimetic scaffolds. Soft Matter 2011, 7, 2918. The insets in both FIGS. 1A and 1B contain inserts that show the collagen scaffold fibrillar structure as revealed by scanning electron microscopy.
Figure 4:
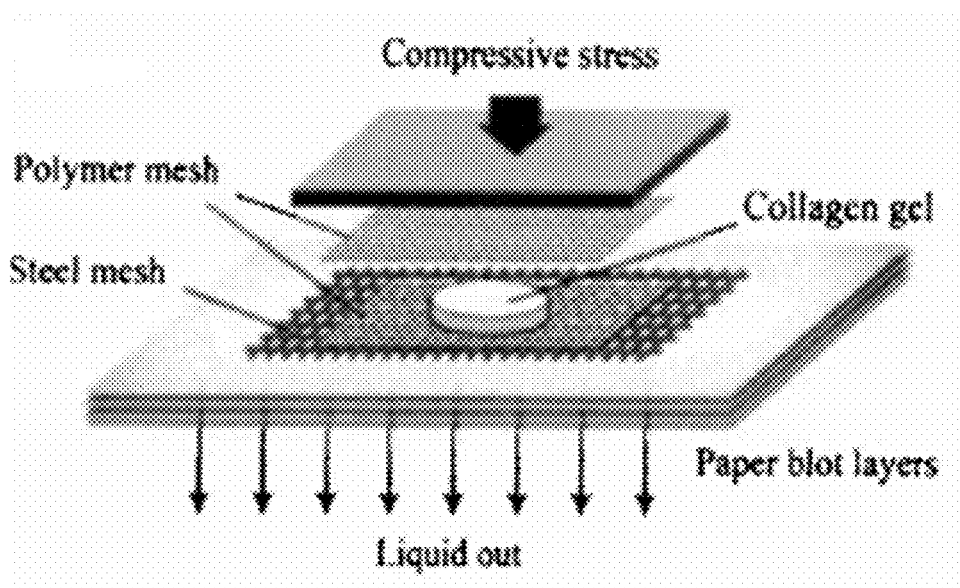
FIG. 4 is a schematic representation of a prior art experimental set-up used to apply varying levels of plastic compression to hydrated scaffolds in order to tune physical-mechanical properties of the patch, adapted from Brown R A, Wiseman M, Chuo C B, Cheema U, Nazhat S N. Ultrarapid engineering of biomimetic materials and tissues: fabrication of nano- and microstructures by plastic compression. Adv Funct Mater 2005; 15:1762-70.

The term "plastic compression" as used herein refers to a method in which biomaterials are produced by providing a gel comprising a matrix of scaffold fibers of and an interstitial fluid; and plastically compacting the gel to produce the biomaterial. By way of example, detailed descriptions of plastic compression are given in the above-referenced Brown et al. WO2006003442 and Serpooshan, Acta Biomateralia and can be seen in FIG. 4 and FIG. 1B, respectively.

The term "scaffold" as used herein refers to a pre-shaped three dimensional article as described herein which can serve as a temporary surrogate for native cell support and can provide a matrix for holding cells, therapeutic compositions, etc.

The term "cardiomyocyte precursor" refers to a cell of a type which differentiates into a mature cardiomyocyte. Such cells may be prepared as described in Xu US 2003/0022367, "Cardiomyocyte precursors from human embryonic stem cells."

Materials and Methods of Examples

Cell Culture and ESC Differentiation

H2B-mCherry EMCs were maintained in DMEM with 10% FBS and antibiotics/antimycotic. Myh6-Puro$^r$;Rex-Blast$^r$ mESCs were generated by Lentiviral transduction and Blasticidin selection, and then cultured. For cardiac differentiation, ESCs were cultured in Iscove's Modified Dulbecco Media (IMDM) supplemented with 10% FBS, 2 mM glutamine, $4.5 \times 10^{-4}$ M monothioglycerol, 0.5 mM ascorbic acid, 200 ug/mL transferrin (Roche), 5% protein-free hybridoma media (PFHM-II, Invitrogen) and antibiotics/antimycotic and differentiated as either embryoid bodies (EBs) formation or monolayer. Puromycin was added at differentiation day 10 for two days to enrich cardiomyocyte. The cells were then trypsinized and plated as monolayer cardiomyocytes. Conditioned media were collected after 2 days culturing of confluent EMC cells and passed through 0.22 um filters (Millipore). Control conditioned media were prepared the same way without EMC cells. Recombinant Fstl1 was purchased from ADIPO BIOSCIENCE.

Ventricular cardiomyocytes were isolated with neonatal rat cardiomyocyte isolation kit (Cellutron) and cultured at 37° C. with 5% CO2. In brief, ventricles were dissected from 1-2-d-old Hsd:SD rats (Sprage Dawley), then digested five times for 15 min each with the enzyme cocktail at 37° C. Cells were pooled, preplated for 90 min on an uncoated dish to remove fibroblasts, and plated on 1% gelatin-coated cell culture plastic dishes in high-serum media (DME/F12 [1:1], 0.2% BSA, 3 mM sodium-pyruvate, 0.1 mM ascorbic acid, 4 mg/liter transferrin, 2 mM L-glutamine, and 5 mg/liter ciprofloxacin supplemented with 10% horse serum and 5% FCS) at $3 \times 10^5$ cells/cm2. After 24 h, media was changed to low-serum medium (same but with 0.25% FCS) and cultured until use.

The cell cycle profile of cardiac cells was analyzed as described. In brief, cells were fixed for 1 h at 4° C. with 0.25% PFA and then permeabilized for 15 min at 37° C. with 0.2% Tween 20 before incubation with α-actinin and secondary antibodies (Alexa 488—conjugated anti-mouse Ig) diluted 1:100 in FACS buffer (PBS with 1% goat serum and 0.1% NaN3). Cells were then stained with 10 µg/ml propidium iodide in FACS buffer supplemented with 500 µg/ml of RNAase A. Flow cytometry was performed on BD FACSCanto. FlowJo and ModFit software were used to analyze the results.

RNA Extraction and Q-RT-PCR

Total RNA was extracted with TRIzol (Invitrogen) and reverse transcribed to cDNA with QuantiTect Reverse Transcription Kit (Qiagen) according to the manufacturer's instructions. cDNA samples synthesized from 100 ng of total RNA were subjected to RT-QPCR with LightCycler 480 SYBR Green I Master kit (Roche) performed with LightCycler 480 Real-Time PCR System (Roche). Primer sequences are listed in Table 1.

TABLE 1

Q-RT-PCR Primers

| Gene (ACCESSION NO.) | Forward Primer | Reverse Primer |
| --- | --- | --- |
| GAPDH | aatggatacggctacagc (SEQ ID NO. 2) | gtgcagcgaactttattg (SEQ ID NO. 3) |
| Myh6 | catgccaatgacgacct (SEQ ID NO. 4) | Cctacactcctgtactgcc (SEQ ID NO. 5) |
| Mlc2v | aggtccaattaacttcaccgt (SEQ ID NO. 6) | Gtcagcatctcccggacata (SEQ ID NO. 7) |
| Mlc2a | accgtcttcctcacact (SEQ ID NO. 8) | cttgtctgcctgggtca (SEQ ID NO. 9) |

LC-MS/MS Analysis of Conditioned-Media

First, tris(2-carboxyethyl)phosphine (TCEP) was added into 1 mL of conditional media to 10 mM and the protein sample was reduced at 37° C. for 30 min. Then iodoacetamide was added to 20 mM and the solution was alkylated at 37° C. for 40 min in dark. Mass Spectrometry Grade of trypsin (Promega) was then added to the solution as 1:100 ratio. After overnight digestion at 37° C., the sample was then desalted using a SepPack cartridge, dried using a SpeedVac and re-suspended in 100 µL of 5% formic acid. The resulting peptides were on-line analyzed by LC-MSMS system, which consist of a Michrom HPLC, a 15 cm Michrom Magic C18 column, a low flow ADVANCED Michrom MS source, and a LTQ-Orbitrap XL (Thermo Scientific, Waltham, Mass.). A 120-min gradient of 0-30% B (0.1% formic acid, 100% acetonitrile) was used to separate the peptides, and the total LC time was 141 min. The LTQ-Orbitrap XL was set to scan the precursors in the Orbitrap at a resolution of 60,000, followed by data-dependent MS/MS of the top 4 precursors.

The raw LC-MSMS data was then directly submitted to Sorcerer Enterprise (Sage-N Research Inc.) for protein identification against the IPI rat protein database, which contains semi-tryptic peptide sequences with the allowance of up to 2 missed cleavages and precursor mass tolerance of 50.0 ppm. A molecular mass of 57 Da are added to all cysteines to account for carboxyamidomethylation. Differential search includes 16 Da for methionine oxidation. The search results are viewed, sorted, filtered, and statically analyzed using PeptideProphet and ProteinProphet (ISB). The minimum trans-proteomic pipeline (TPP) probability score for proteins and peptides was set to 0.95, respectively, to assure TPP error rate of lower than 0.01.

Atomic Force Microscopy—Microstiffness Assessment

In order to assess the mechanical coupling of the produced collagen patches with native myocardium, microstiffness of plastic compressed collagen gels were measured via utilizing an atomic force microscope (AFM) in nano-indentation mode. A custom-made flat AFM tip was manufactured using electron beam deposition and utilized to probe the stiffness of the gels in scanning areas of 90 µm×90 µm.

Calcium Imaging

Kinetic Image Cytometer from Vala was used as instructed to record intracellular calcium transient with Fluo4 NW calcium indicator (Life Science). Data was processed using Cyteseer (Vala).

Echocardiography

In vivo heart function was evaluated by echocardiography two and four weeks after LAD ligation. Two-dimensional (2D) analysis was performed on mice using a Sonos 5500 ultrasonograph with a 15-MHz transducer (Philips, Andover, Mass., USA). The mice were sedated with isoflurane (100 mg/kg, inhalation), and the chest was shaved. The mice were placed on a heated platform in the supine or left lateral decubitus position to facilitate echocardiography. 2D clips and M-mode images were recorded in a short axis view from the mid-left ventricle at the tips of the papillary muscles. LV internal diameter (LVID) and posterior wall thickness (LVPW) were measured both at end diastolic and systolic. Fractional shortening (FS, %) and ejection fraction (EF, %, via extrapolation of 2D data) were calculated from LV dimensions in the 2D short axis view.

In Vivo Delayed-Enhanced Magnetic Resonance Imaging (DEMRI)

To prepare for scanning, induction of anesthesia was accomplished with 2% and maintained with 1.25-1.5% isoflurane with monitoring of the respiratory rate. ECG leads were inserted subcutaneously to monitor the heart rate while the body temperature was maintained at 37° C. Using 3T GE Signa Excite clinical scanner with a dedicated mouse coil (Rapid MR International, Germany), functional parameters were recorded on weeks 1 and 4 after treatment. The following sequences were performed for MRI acquisitions: (1) DEMRI was performed following IP injection of 0.2 mmol/kg gadopentetate dimeglumine (Magnevist, Berlex Laboratories) using gated fGRE-IR sequences with FOV 3.4 cm, slice thickness 0.9 mm, matrix 128×128, TE 5 ms, TI 150-240 ms, and FA 60°; and (2) cardiac MRI of volumes were performed using fSPGR with FOV 7 cm, slice thickness 0.9 mm, matrix 256×256, TE 5.5 ms, and FA 30. Coronal and axial scout images were used to position a 2-dimensional imaging plane along the short axis of the left ventricular (LV) cavity.

MRI Image Analysis

MRI image analysis was performed as described previously. Briefly, for each short-axis slice, planimetry measurements of LV myocardial area were conducted off-line by tracing the epicardial and endocardial borders at end systole and end diastole with OsiriX software (OsiriX, open-source). For these purposes, the papillary muscles were considered part of the LV cavity. Left ventricular mass (LVM), LV end-diastolic volume (LVEDV), and LV end-systolic volume (LVESV) were measured to calculate the LV ejection fraction (LVEF). For infarct analysis, the DEMRI enhanced area was designated as scar tissue. These areas were traced in short-axis slices and integrated to determine scar volumes by DEMRI in mice hearts (n=4). The % DEMRI scar volume=(DEMRI scar volume/total LV mass volume)×100.

Histology and Immunohistochemistry

Histological analysis was performed according to standard protocols for paraffin embedding. For immunohistochemistry, embedded embryos were sectioned at a thickness of 7 µm, unless described otherwise. Antibodies used were as follows: 1:200 α-actinin (Sigma, A7811), 1:100 phospho-Histone3 (Millipore 06-570), 1:100 WT1 (Abcam, ab15249).

EXAMPLES

Example 1: Epicardial Factors for Use in Patch to Activate Cardiogenesis

Figures 2A, 2B:
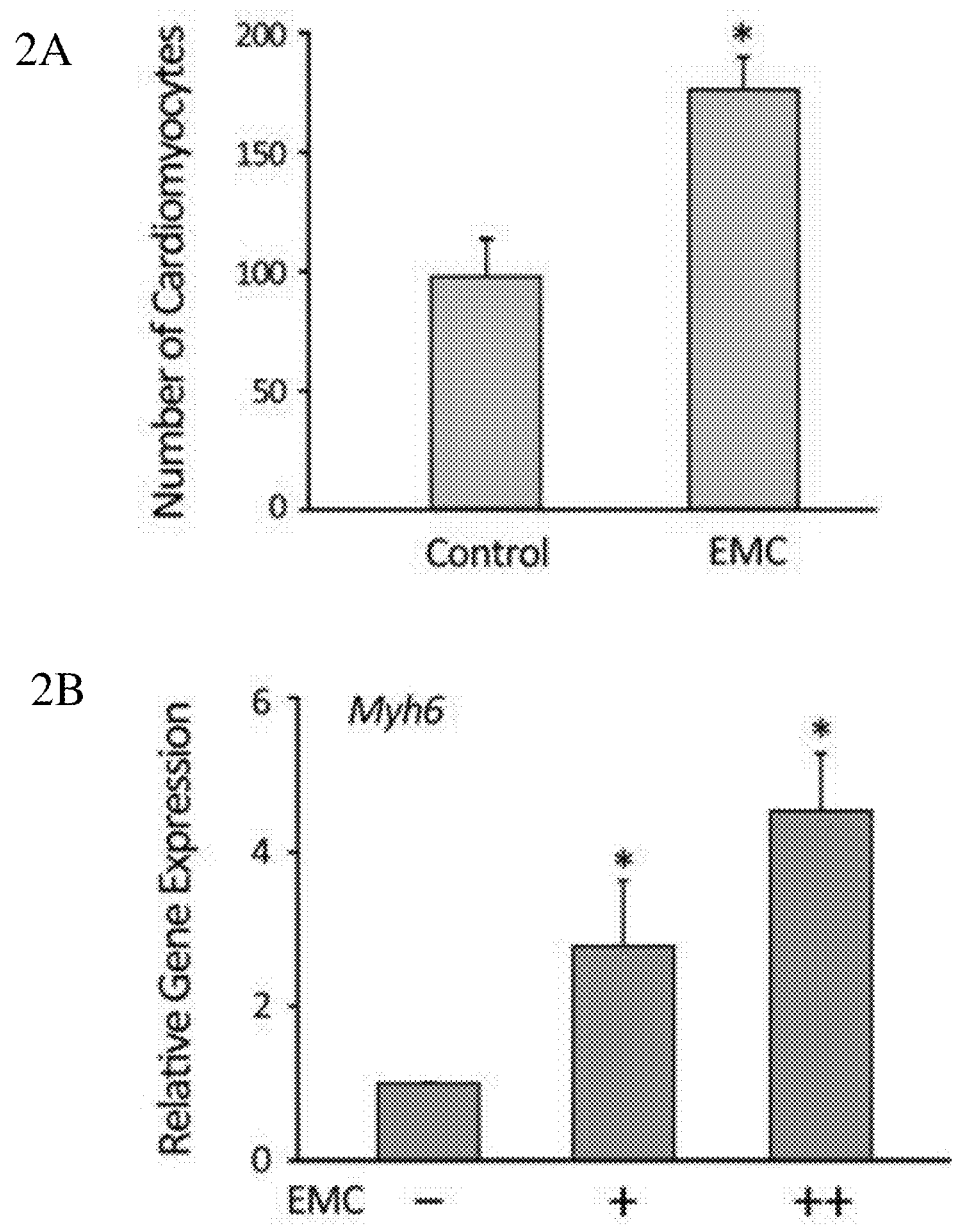
FIGS. 2A and 2B is a pair of graphs showing the effect of epicardium-myocardium co-culture on cardiogenesis.

We utilized an epicardial/mesothelial cell line (EMC) to investigate the interaction between epicardium and myocardium. Mouse Embryonic Stem Cell (mESC)-derived immature cardiomyocytes (day 2 after the onset of αMHC expression, hereonto mCM-d2) co-cultured with EMCs (see Methods) yielded significantly greater number of α-actinin$^+$ cells (FIG. 2A) and increased expression of the cardiomyocyte marker Myh6 (FIG. 2B) compared to mESCs culture in standard differentiation media; thus suggesting that epicardial cells enhance cardiomyogenesis. This enhancement was recapitulated by replacing co-culture with EMC-conditioned media (hereonto epicardial-conditioned media). mCM-d2 treated for 8 days with epicardial-conditioned media demonstrated increased cardiogenesis, as indicated by the number of cells expressing α-actinin (FIG. 3A) and their content in cardiomyocyte-specific mRNAs including Myh6, Mlc2v and Mlc2a (FIG. 3B). At the functional level, mCM-d2 treated with epicardial-conditioned media presented significantly greater number of cells with rhythmic calcium transient (i.e. more beating cells) than those cultured with standard media, as indicated by Kinetic Image Cytometry (KIC) (FIG. 3C).

Example 2: Preparation of Engineered Collagen Patches Exert a Positive Effect on Cardiac Function after Injury Cardiac Patch Highly hydrated collagen gels—used as cardiac patch—were produced by adding 0.5 and 0.6 ml of 10× and 1×DMEM (Sigma, MO, US), respectively, to 0.9 ml of sterile rat tail type I collagen solution in acetic acid (3.84 mg/ml, Millipore, Mass., US) and neutralizing with 5 M NaOH. In the case of patches containing epicardial factors, the EMC culture media was collected after 3 days (confluent cells), filtered, and replaced with the 1×DMEM in the protocol above. Prepared collagen solution (0.9 ml) was then distributed into 24-well plates (15.6 mm in diameter) and placed in a tissue culture incubator for 30 min at 37° C. for polymerization. Plastic compression (PC) of highly hydrated collagen gels has recently been developed as an engineering approach for the rapid production of biomimetic scaffolds. Maintaining the cells viability, PC significantly improves the mechanical properties of the gels, as well as cell metabolic activity, differentiation, and remodeling.

Myocardial Infarction and Patch Implantation in Mice

Male 10-12 weeks old C57BL/6J mice were purchased from Jackson Laboratories (Bar Harbor, Me., USA). The entire procedures in this study, involving animal use and surgeries, were approved by the Stanford Institutional Animal Care and Use Committee (IACUC). Animal care and interventions were provided in accordance with the Laboratory Animal Welfare Act. Mice were anesthetized using an isoflurane inhalational chamber, endotracheally intubated using a 20-gauge angiocatheter (Ethicon Endo-Surgery, Inc, Cincinnati, Ohio), and connected to a small animal volume-control ventilator (Harvard Apparatus, Holliston, Mass.).

Figures 6A, 6B:
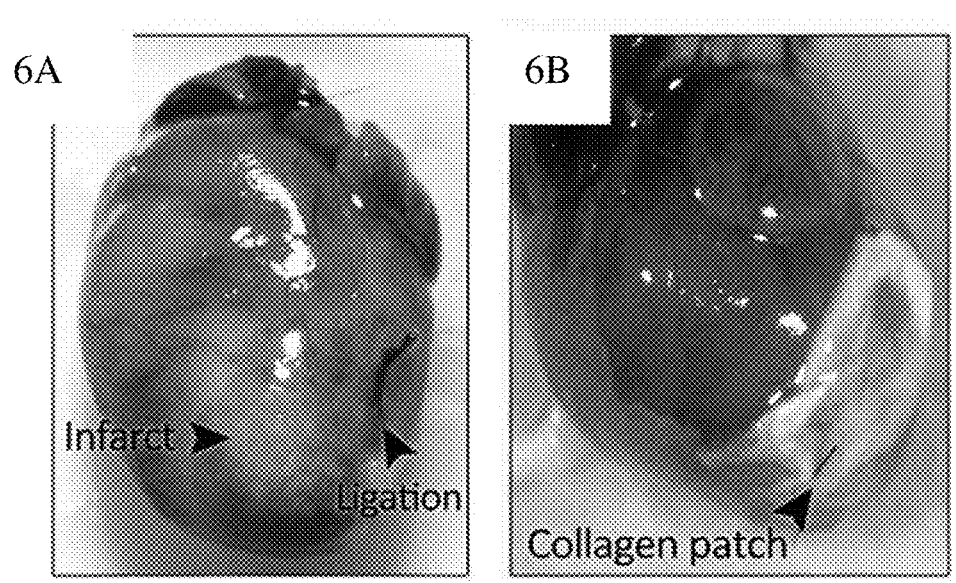
FIGS. 6A and 6B is a pair of photographic images showing (A) a myocardial infarction and (B) patch implantation in the mouse hearts.

A left thoracotomy was performed via the fourth intercostal space and the lungs retracted to expose the heart. After opening the pericardium, a 7-0 suture was placed in the anterior myocardium to occlude the left anterior descending artery (LAD) near its origin between the pulmonary outflow tract and the edge of the left atrium (FIG. 6A). Ligation was considered successful when the LV wall turned pale. In the case of experimental groups treated with patch, immediately after the ligation, prepared collagen patch was sutured at two points (FIG. 1A, FIG. 6B) onto the surface of ischemic myocardium.

Animals were kept on a heating pad until they recovered. Another group of mice underwent sham ligation; they had a similar surgical procedure without tightening the suture around the coronary arterTo examine whether factors secreted from epicardial cells have an effect in vivo, we engineered a collagen patch to mimic the physical-mechanical properties of the epicardium and its border zone with the myocardium. For this purpose, collagen gels were subjected to plastic compression (PC). Varying levels of PC were applied in order to tune physical-mechanical properties of the patch. In this case, an application of static compressive stress of 690 Pa was applied to the cast gel for 2 minutes.

Figures 5A, 5B:
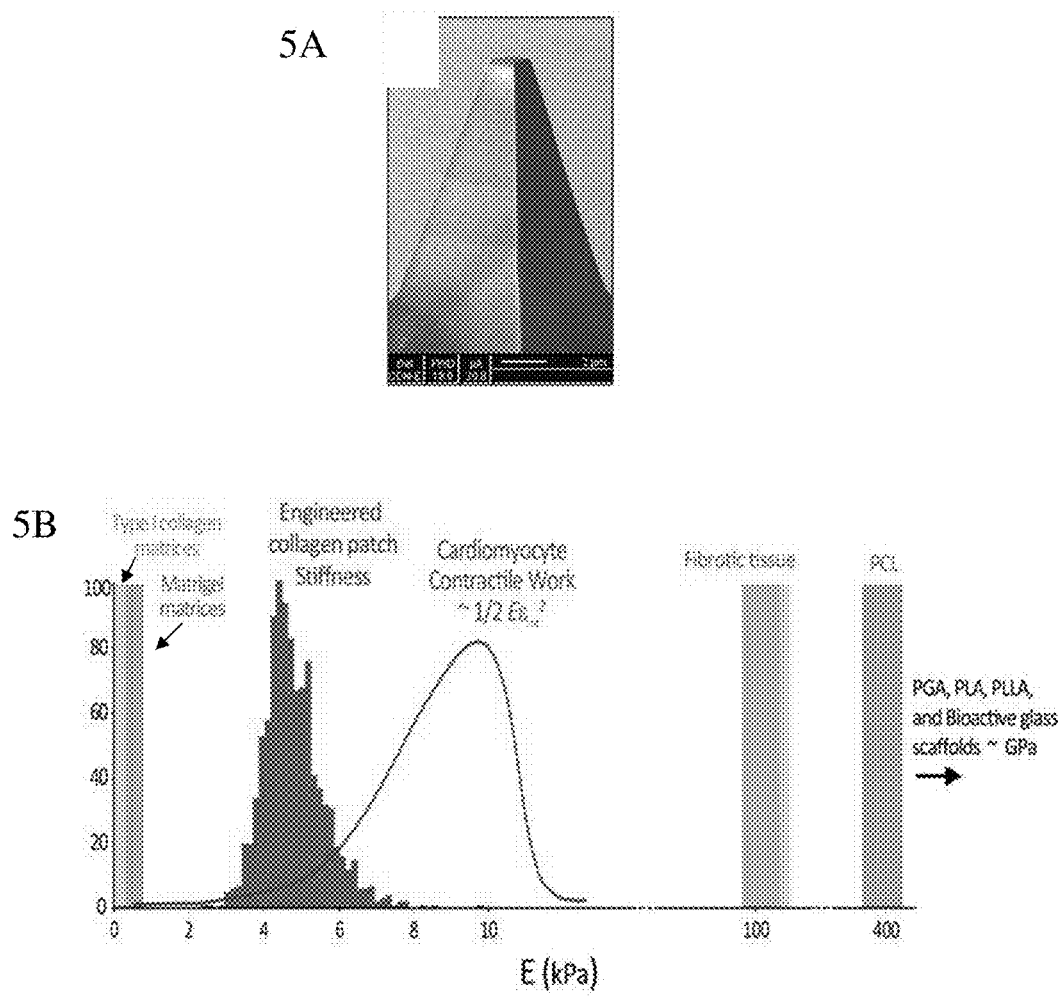
FIGS. 5A and 5B is an image and a histogram showing the evaluation of the mechanical properties of the engineered patch.

Atomic force microscopy (AFM) using a 2 µm-wide flat tip (constructed using electron beam deposition technique, FIG. 5A) was employed to probe microstiffness of the produced collagen patch (90×90 µm surface area). Comparing the measured stiffness values of the collagen patch (~1-10 kPa) with the optimal range of the substrate elasticity that yields the maximum cardiomyocyte contractile work (~1-14 kPa) demonstrates the great potential of the produced collagenous patch to host and culture cardiac cells in vivo (FIG. 5B).

Figure 7:
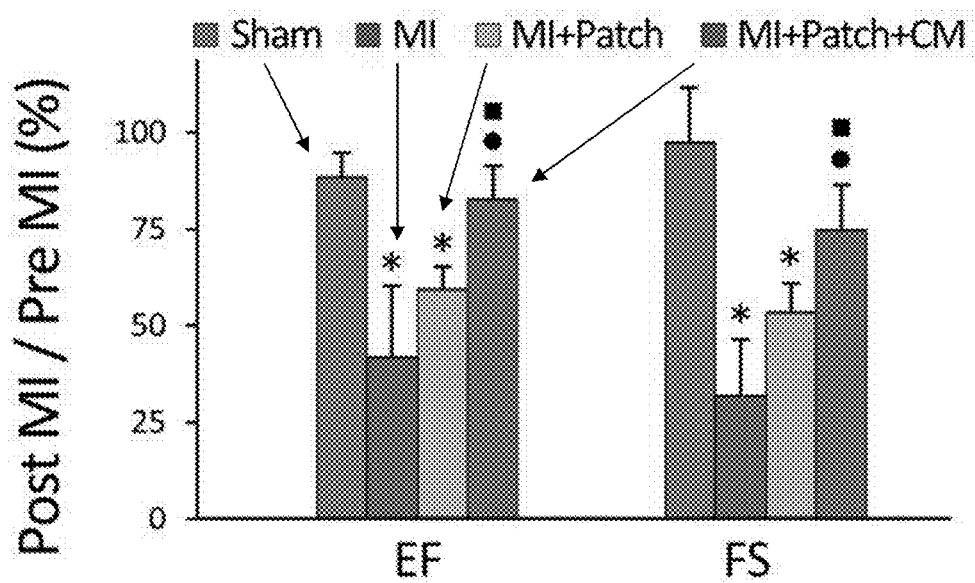
FIG. 7 is a graph showing the summary of echocardiography analysis on all animal groups (mice), including sham, myocardial infarcted (MI), infarcted mice with patch-only implanted (MI+patch) and infarcted animals with patch embedded in epicardial conditioned media (MI+patch+CM).

Immediately post myocardial infarction (MI), collagen patches loaded with epicardial conditioned-media were applied onto the surface of the infarcted area in adult murine hearts (FIG. 6A-6B). Two weeks after MI, hearts treated with patch-conditioned media (Patch+CM) showed significantly preserved ejection fraction (EF) and fractional shortening (FS) (FIG. 7), when compared to non-treated infarcted animals (MI-only) and infarcted animals grafted with patch alone (Patch-only). Preservation of contractility correlated with anatomical features, including noticeable reduced infarct size and remodeling, as was seen by trichrome-stained heart sections (data not shown). These data suggest that epicardial secreted factors embedded within the engineered collagen patch exert a positive in vivo effect on cardiac function post injury.

Example 3: Identification of Epicardial-Derived Cardiogenic Factors for Use with Patch Mass spectrometry was used to analyze the protein content in epicardial-conditioned media obtained from the EMC cells (Table 2).

TABLE 2

List of factors secreted by EMC

| Name | Total independent spectra |
| --- | --- |
| Igfbp2 (Insulin-like growth factor-binding protein 2) | 21 |
| Prss1 (Anionic trypsin-1) | 9 |
| Clu (Clusterin) | 7 |
| Fstl1 (Follistatin-related protein 1) | 7 |
| Ogn (osteoglycin) | 7 |
| Timp2 (Metalloproteinase inhibitor 2) | 6 |
| Pxdn (peroxidasin) | 6 |
| Sparc (SPARC, osteonectin) | 5 |
| C1r (complement C1r subcomponent) | 5 |
| Igfbp7 (Insulin-like growth factor binding protein 7) | 5 |
| Olfml3 (olfactomedin-like 3) | 4 |
| Metrnl (Meteorin-like protein) | 3 |
| Serpinf1 (Serine (Or cysteine) peptidase inhibitor, clade F, member 1) | 3 |
| Bmp1 (bone morphogenetic protein 1) | 3 |
| Pdgfa (Platelet-derived growth factor subunit A) | 2 |
| Crip2 (Cysteine-rich protein 2) | 2 |

Figure 8:
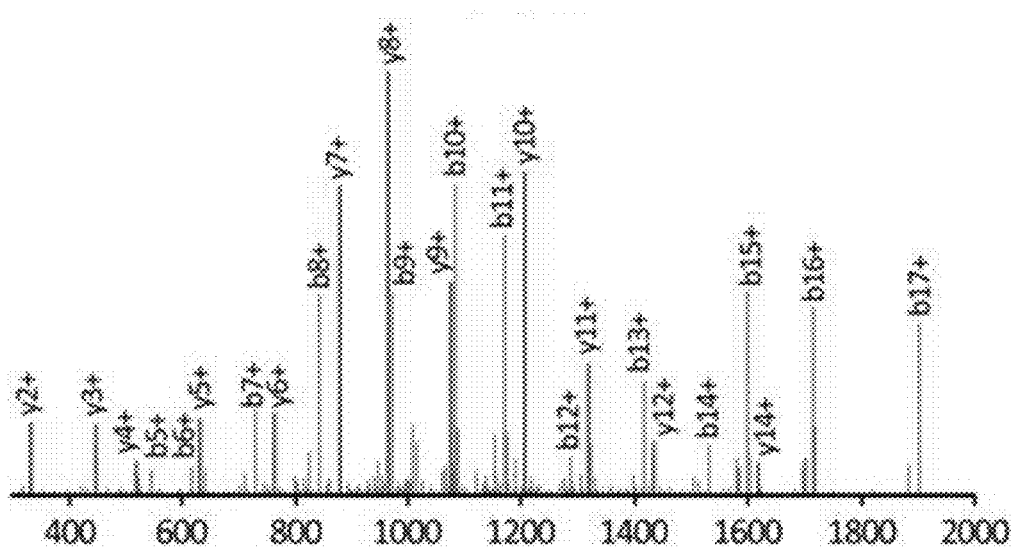
FIG. 8 is a MS/MS spectrum of a fragment between R194 and L 223 one of the peptides identified as Fstl1. See SEQ ID NO: 1 for complete sequence) Peptide probability=1.0, Xcorr=6.276, delta Cn=0.471.
Figures 9A, 9B, 9C:
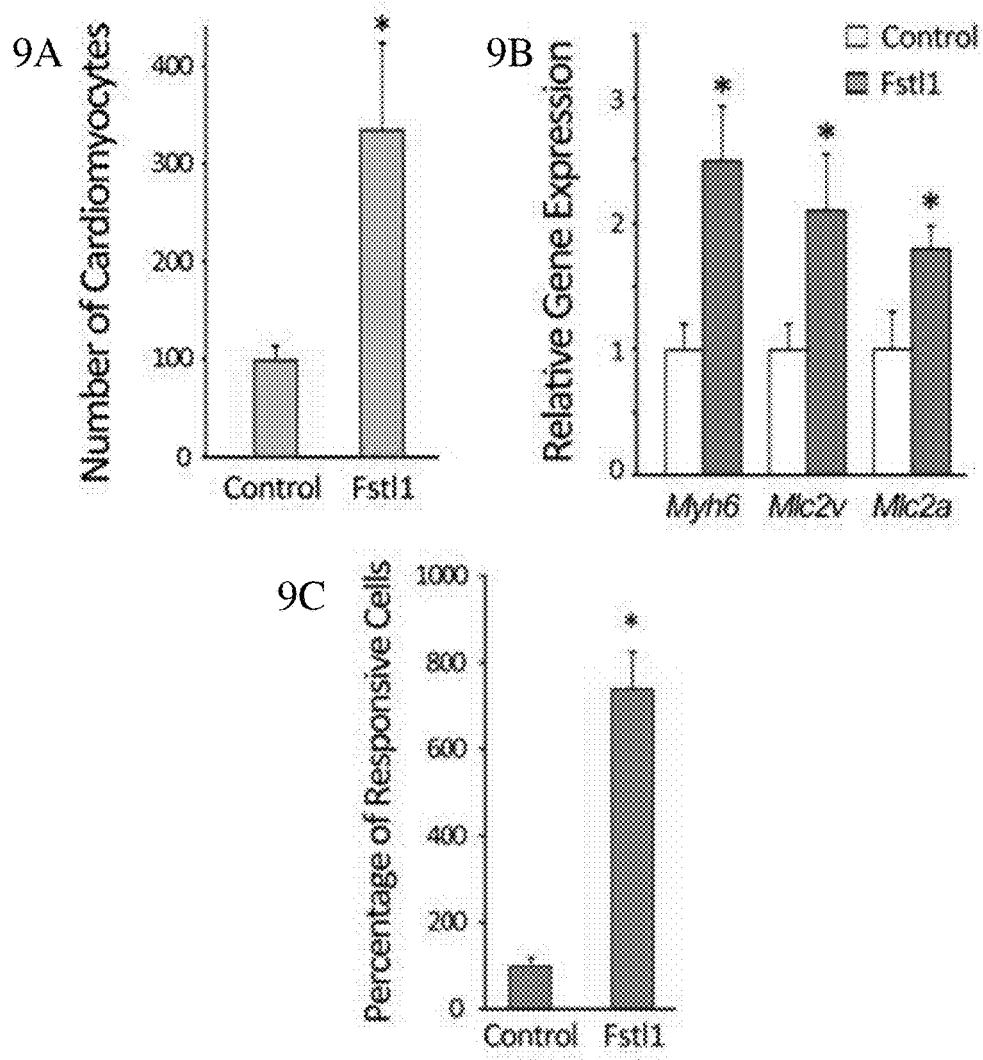
FIGS. 9A, 9B, and 9C is a set of graphs showing the effect of purified Fstl 1 on cardiogenesis of embryonic stem cell-derived cardiomyocytes.

We identified five unique peptides in a total of seven spectral counts that are located in the sequence of Follistatin-like1 (Fstl1) (FIG. 8). Direct visualization of the Fstl1 protein showed that this peptide is expressed in embryonic and adult epicardium under normal conditions. Fstl1 expression is dynamic in conditions of injury. In the case of MI, Fstl1 is upregulated in the infarcted myocardium, while it becomes depleted in the epicardium (data not shown). Although recent reports indicate that Fstl1 has an activity in the cardiovascular system, this could go both ways: as a cardio-protective agent upon Fstl1-viral induction through activation of the AKT pathway in the cardiomyocytes, or as a biomarker since elevated serum fstl1 in patients with heart failure was associated with LV hypertrophy. There has been yet no report on the potential role of epicardial Fstl1 in cardiac regeneration.

We applied 10 ng/ml purified hFstl1 onto the mCM-d2 system of ESC-derived early cardiomyocytes, similarly to the coculture and conditioned media experiments described in FIG. 2. Eight days of treatment with Fstl1 resulted in a significant increase (4-fold) in the number of cardiomyocytes, increased 2-3 folds the mRNA content of contractile proteins (including Myh6, Mlc2v, and Mlc2a, FIG. 2H), and increased 7-8 folds the number of cardiomyocytes displaying rhythmic calcium transient (KIC analysis) (data not shown). These results suggest that Fstl1 possesses the major cardiogenic function of the epicardial secretome.

The potential activity of Fstl1 was subsequently tested in vivo. For that purpose, 10 ug Fstl1 were added to each collagen patch prior to polymerization and plastic compression (in liquid state). C57/BL6 mice were subjected to MI and treated immediately with collagen patch with or without Fstl1 (Patch-only and Patch+Fstl1, respectively). Echocardiography and magnetic resonance imaging (MRI) analyses were utilized to assess the morphology and functionality of the injured hearts. Two weeks post MI, significant improvement was observed in the cardiac structure and function of both Patch-only and Patch+Fstl1 groups (compared to MI-only), while there was no significant difference between these two groups.

Figure 10A:
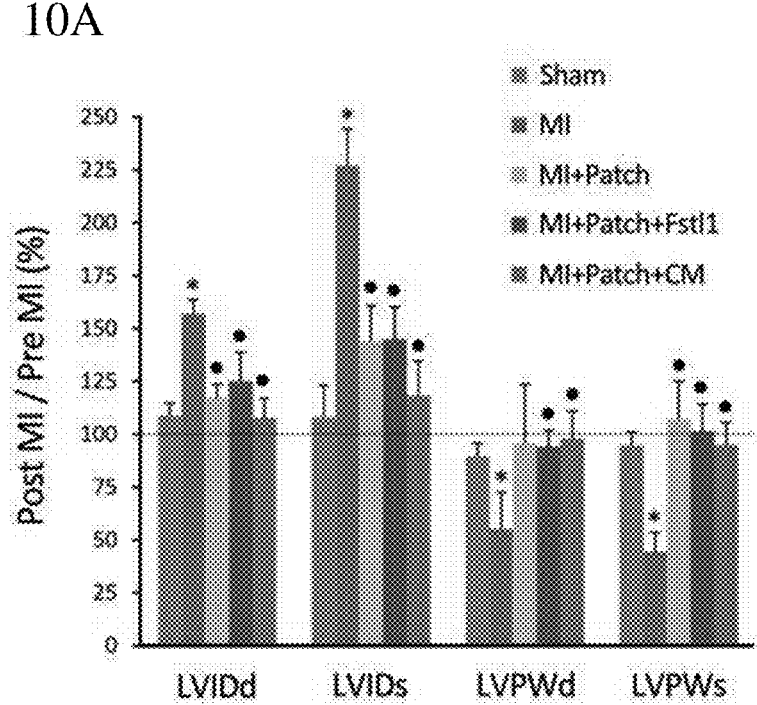
FIGS. 10A and 10B is a pair of graphs showing echocardiographic analysis of different animal groups 4 weeks post MI.
Figure 10B:
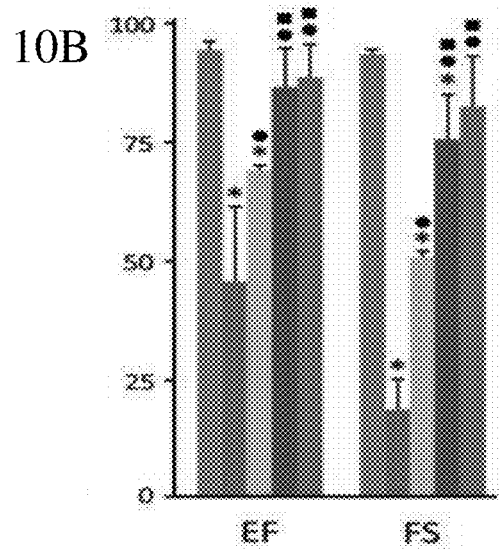

Heart function enhancement continued to increase in the Patch+Fstl1 group, four weeks post implantation, exhibiting a statistically significant increase in contractility (EF and FS) compared to the MI-only and Patch-only groups (FIG. 10A-10B). Results indicated significant decrease in LV dilation and increase in LV posterior wall thickness in all of the patch-treated hearts. As stated above, cardiac function (EF and FS) was improved significantly in the treated hearts, while the Patch+Fstl1 and Patch+CM showed the greatest enhancement. Improvement in contractility was accompanied by structural preservation of the Patch+Fstl1-treated hearts, as shown by the decrease in the LVIDd and LVIDs (~20 and 36% reduction, respectively), and an increase in LVPWd and LVPWs (~71 and 130%, respectively). Patch+Fstl1 and Patch+CM groups showed the highest levels of EF and FS which were significantly greater than those in the Patch-only group. Thereupon, Patch-Fstl1 implantation effectively interfered with the post-MI remodeling processes in the LV, including diminishing the LV dilation and wall thinning.

Figure 11A:
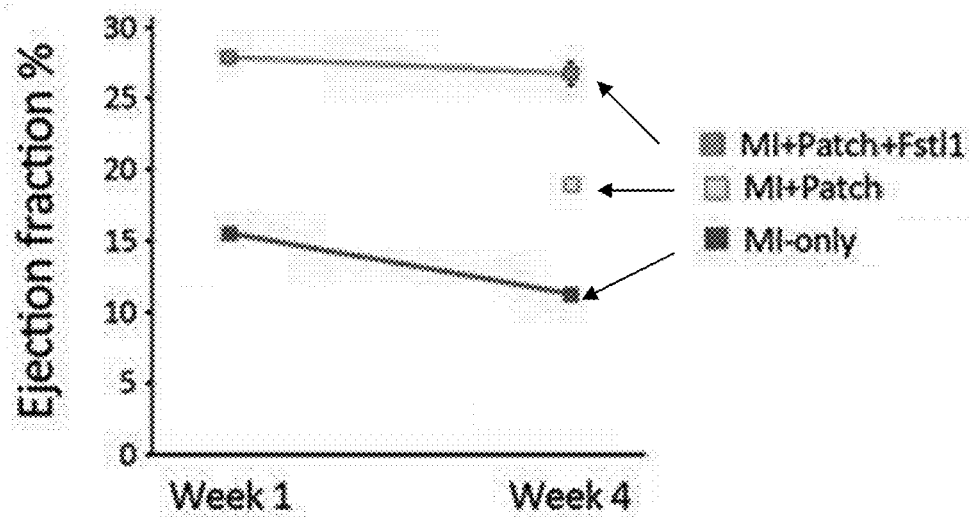
FIGS. 11A and 11B is a pair of graphs showing quantification of ejection fraction and scar volume ratio from the MRI data. These data confirmed the echo results, demonstrating the significant effect of patch improvement and Fstl1 in improvement of cardiac function and decreasing the scar size.
Figure 11B:
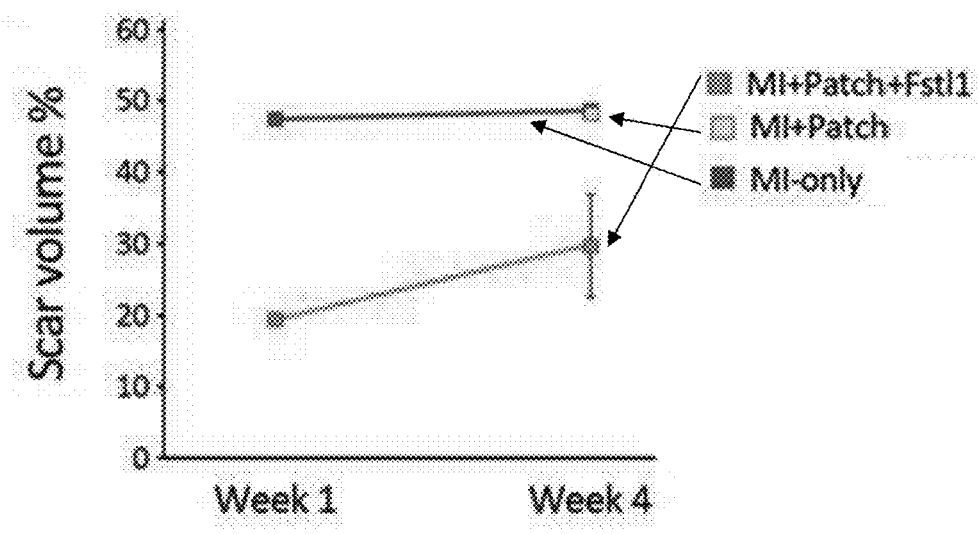
Figures 12A, 12B:
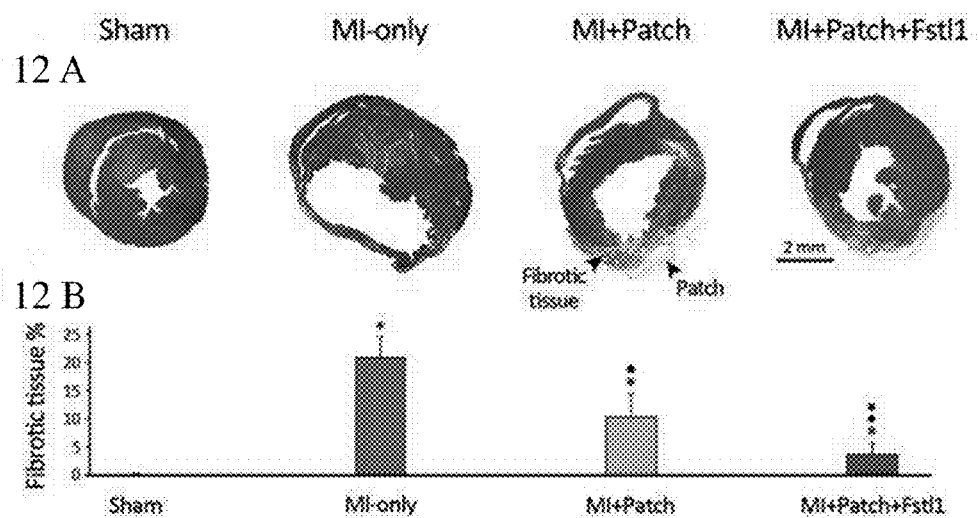
FIGS. 12A and 12B is a set of images and a graph showing histological analysis.
Figures 13A, 13B:
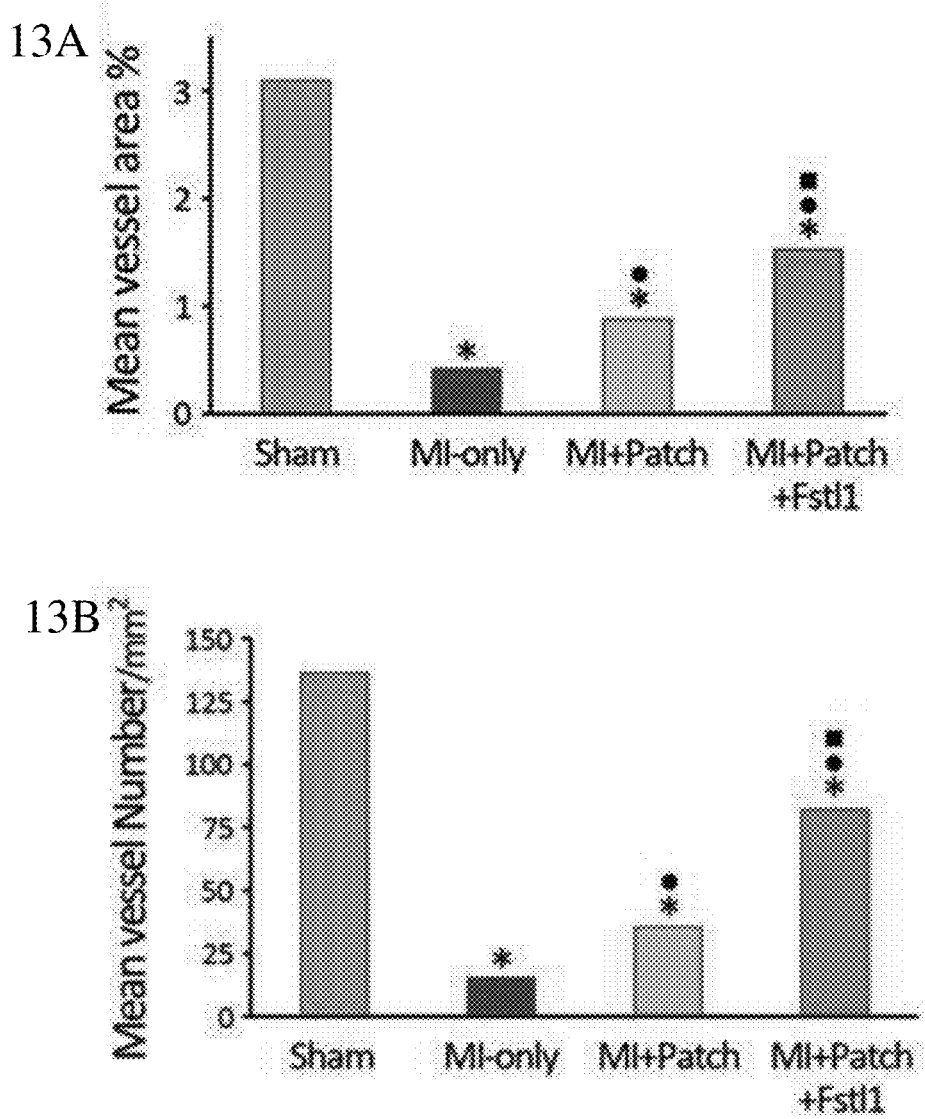
FIGS. 13A and 13B is a pair of graphs showing the quantification of blood vessel density (mean vessel area % (A) and mean vessel number/$mm^2$ (B)) in different animal groups, as calculated using the von Willebrand factor staining images (n=60).

MRI analysis of cardiac function in an independent experimental group of animals, utilizing gadolinium contrast agent, confirmed that while application of patch, alone, enhanced cardiac function (EF) from ~11% (in MI-only) to ~19%, addition of Fstl1 resulted in an additional ~9% significant improvement in EF (reaching ~28%) and a decrease in scar volume (from ~49% to ~30%, FIG. 11A-11B). In sum, Patch+Fstl1 treatment over the time course of four weeks resulted in more than doubling of the EF compared to MI-only mice. Histological analysis demonstrated attenuated fibrosis (FIG. 12A-12B) and increased vascularization (FIG. 13A-13B), both qualitatively and quantitatively, in all of the patch-grafted hearts, while the Patch+Fstl1 group yielded the lowest fibrotic tissue % (~3.7%) and the greatest vessel density values (~1.5% mean vessel area and ~82 vessels/mm$^2$).

Immunofluorescent analysis of sham and MI-only hearts confirmed the depletion of Fstl1 from the epicardium, four weeks post MI (data not shown). While Patch-only group exhibited dramatically lower amount of Fstl1, it was still richly detectable in the Patch+Fstl1 group (data not shown), suggesting that the effect of Fstl1 is not acute. α-actinin$^+$ striated cardiomyocytes were found within the patch in the Patch+Fstl1 group, but not in the Patch-only group (data not shown), suggesting cardiomyocyte regeneration is induced by Patch+fstl1. Strikingly, a significantly greater number of phospho-Histone3$^+$/α-actinin$^+$ cells were observed in the border zone of Patch+Fstl1 hearts, further suggesting the regeneration of cardiomyocytes is still active 4 weeks after MI in Patch+Fstl1 group.

Figure 14A:
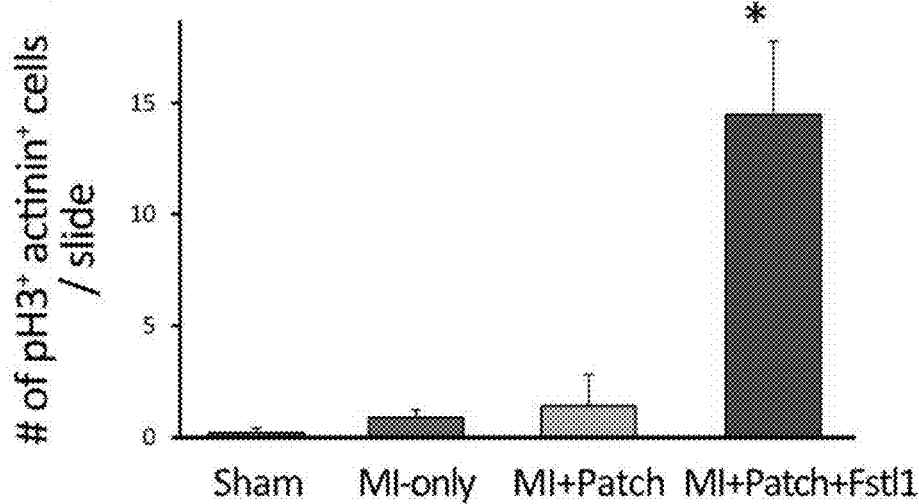
FIGS. 14A and 14B is a pair of graphs showing the quantification of phospho-Histone3$^+$/α-actinin$^+$ and WT1$^+$ cells in four groups.
Figure 14B:
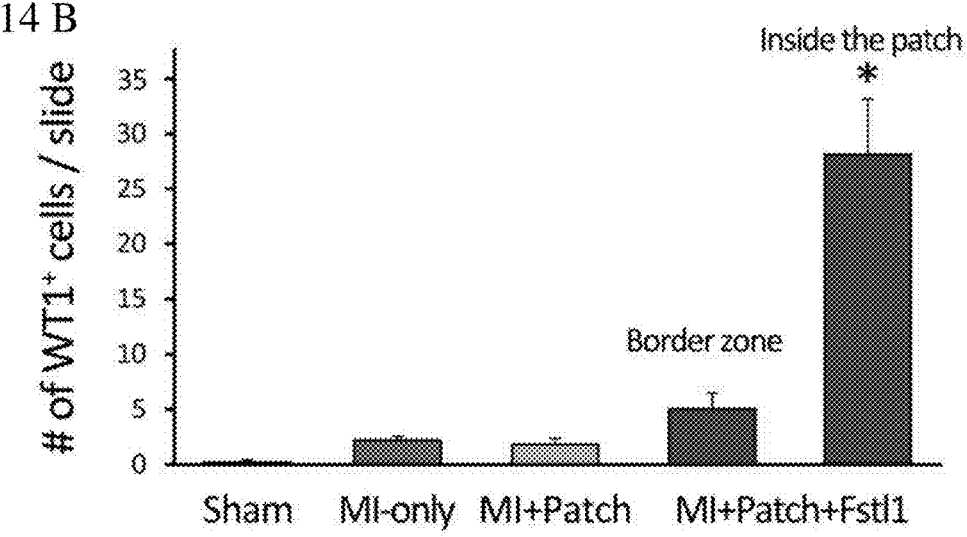
Figure 15:
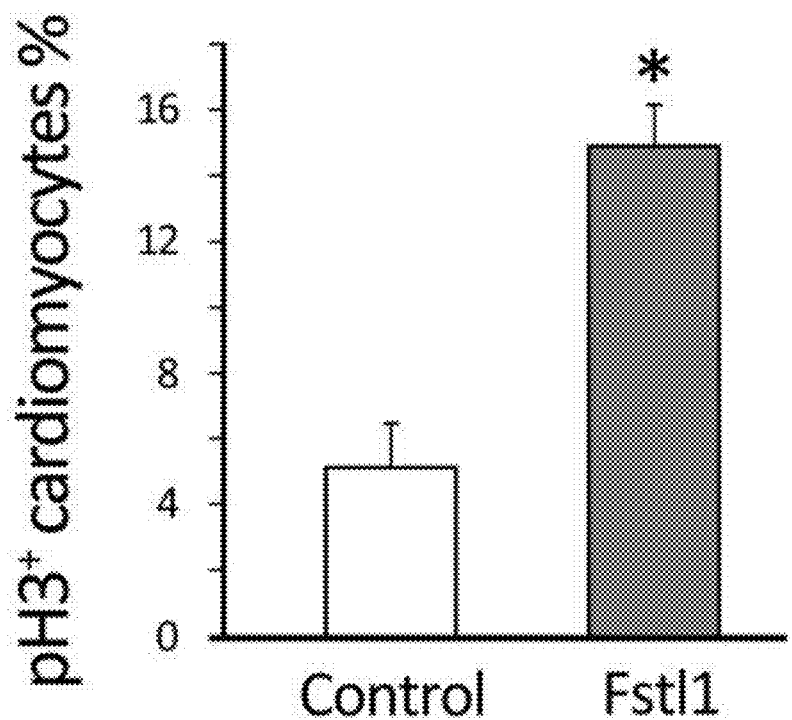
FIG. 15 is a graph showing the quantification of cardiomyocytes with or without fstl1 treatment.

To corroborate with the finding in vivo, mCM-d2 were treated with Fstl1 for 48 hrs and significantly more phospho-Histone3$^+$ cells were found in the Fstl1 treated group (FIG. 14A-14B, FIG. 15), suggesting that Fstl1 directly induces proliferation of cardiomyocytes. Neonate Rat Ventricular Cardiomyocytes (NRVC) treated with Fstl1 for 24 hours showed significantly increased percentage of cells in S/G2/M phase (data not shown), confirming the direct pro-proliferation effect of Fstl1 on cardiomyocytes.

Example 4: Identification of FSTL1 as Epicardial-Secreted Cardiogenic Activity

Figures 16A, 16B, 16C:
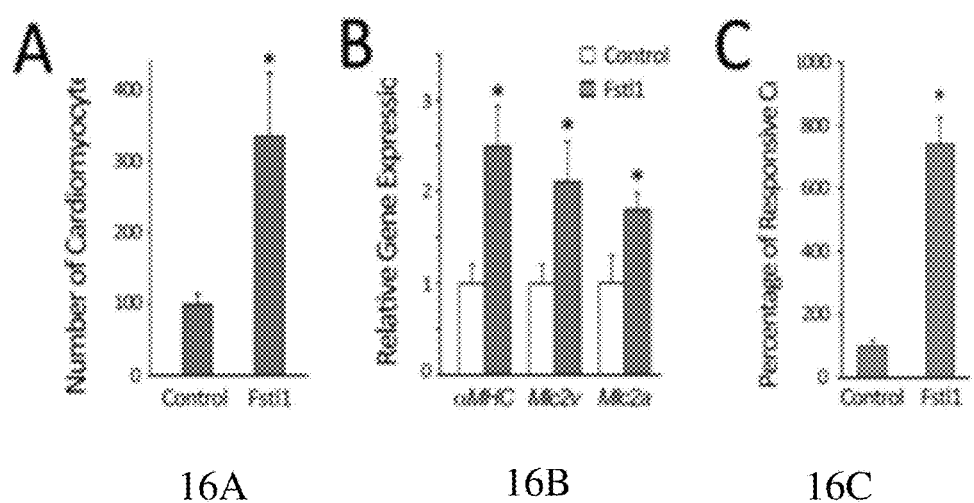
FIGS. 16A, 16B and 16C is a series of graph showing the effect of recombinant FSTL1 on mESC-derived cardiomyocytes. mESC-derived cardiomyocytes (mCM-d2) were cultured with recombinant FSTL1.

Referring to FIG. 16, mESC-derived cardiomyocytes (mCM-d2, embryonic stem cell-derived cardiomyocytes) were cultured with recombinant FSTL1. FIG. 16A shows a number of β-actinin positive cells per plate in mCM-d2 cultures with or without FSTL1 treatment (n=8). FIG. 16 B shows expression of cardiac-specific markers in mCM-d2 after 8 days of treatment in FSTL1, normalized to Gapdh expression (n=3). FIG. 16 C) shows a number of cardiomyocytes/plate with rhythmic calcium transients. Contractile Ca2+ transients recorded automatically (n=6 biological replicate samples, each >200 cardiomyocytes) * ($p<0.05$)

We next probed the source of the pH3-Ser10$^+$ cardiomyocytes in the Patch+Fstl1 treatment group by lineage-labeling pre-existing cardiomyocytes using the well-characterized reporter system αMHCmerCREmer:Z/EG that uses a tamoxifen-inducible Cre under the control of the cardiomyocyte-specific αMHC promoter to label αMHC$^+$ cells before the MI (data not shown). As known, the phosphorylation of histone H3 at Ser10 (pH3) only occurs in cells undergoing mitosis, making pH3 a marker for labeling proliferating cells.

Reporter mice were treated with 4-OH-tamoxifen (OH-Tam) for 7 days (~3 to −2 weeks before LAD ligation surgery to allow for 4-OH-tam clearance). Animals analyzed 4 weeks post-MI displayed eGFP$^+$, pH3-Ser10$^+$ double positive cells the border zone (data not shown). No eGFP$^+$ cardiomyocytes were pH3-Ser10$^+$ remote from the infarct area, indicating a localized effect. Furthermore, no eGFP$^+$, pH3-Ser10$^+$ cardiomyocytes were detected in Patch+MI or MI alone groups (although pH3-Ser10$^+$ non-cardiomyocytes were detected), indicating dependence on FSTL1. The data are consistent with the model that FSTL1 induces proliferation in cells that had expressed αMHC (cardiomyocytes) during the window of 4-OH-tam treatment prior to MI.

Example 5: Differentiation Stage-Dependent Effects of FSTL1

Next, the scoring of cell-cycle re-entry and cytokinesis in response to FSTL1 is performed. Cultured cells are analyzed for evidence of cell cycle entry and, importantly, cell division using EdU incorporation (S-phase), pH3Ser10 immunostaining (entry into mitosis), anillin-eGFP localization to midbody (indicative of cytokinesis), aurora B kinase localization [indicative of mitosis and cytokinesis (midbody)], TUNEL staining (apoptosis). Co-localization with progenitor (Nkx2.5, c-kit) and cardiomyocyte (α-actinin, cTnT, myosin), smooth muscle (smMHC, aSMA), endothelial (CD31/Pecam1, V-cam) markers identify the cell types.

Activation of cardioprotective signaling in response to FSTL1 is then analyzed. The AKT and AMPK pathways are predominantly cardioprotective, highly linked to cell metabolism, and has been described as part of the FSTL1-mediated response. Here, the above-described cultures are used with a different readout, immunoblotting for activated signaling proteins: phosphor-AKT and phosphor-AMPK, as well as examination of phosphorylation/activation of downstream targets (e.g. glycogen-synthase kinase-3 beta and S6 kinase). We also collected mRNA to analyze for markers of hypertrophy (ANF, α/βMHC) that might change during the treatment.

Example 6: Intracellular Mediators of FSTL1 Responsible for Survival and Proliferative Responses This example describes readouts used to determine downstream signaling involved in differential signaling from FSTL1. By identifying molecular markers for FSTL1 action, one can identify potential targets for drugs to mimic the beneficial effects of FSTL1 in the survival and proliferation of cardiomyocytes.

In one approach, whole transcriptome profiling after long and short term treatment is used. Transcriptome profiling is a common approach to gain insight into signaling pathways through the analysis of pathway selective gene expression.

Responsive cells selected in the previous experiments are incubated with FSTL1 for 24 hours (short-term) or 7 day (long-term). Transcripts are profiled using microarrays (Affymetrix). Candidate factors are then validated functionally using small molecule inhibitors (if available) and/or siRNA.

Experiments were conducted to analyze the proliferative response of early cardiomyocytes to FSTL1. 7 days following FSTL1 treatment, we observed that a remarkable 50% of the differentially expressed transcripts are known targets of the JAK/STAT and interferon related (IFR) pathways. In addition, we screened a small library of compounds that target signal transduction pathways (from EMD StemSelect) and found that inhibitors of STAT1/2 signaling blocked FSTL1-induced proliferation (e.g. JAK2 inhibitor WP1066; See FIG. 15). These data suggest that a key signaling mediator of the FSTL1 proliferative response in immature cardiomyocytes is STAT1/2.

Example 7: Delivery of Patch with FSTL1 to Activate Myocardial Healing and or Regeneration It has been found that implantation of the FSTL1 patch shortly after a complete coronary occlusion elicited a beneficial effect. Key variables, including time of delivery and the effectiveness following reperfusion. A second critical issue concerns the localized site of FSTL1 delivery. Systemic delivery was not effective in the mouse MI model, compared to epicardial-localized delivery. However, the present the epicardial biomaterial patch itself may provide an effective physical support that could synergize with a systemic FSTL1 delivery. FSTL1 must be delivered epicardial to be effective, and may done by impregnated into the collagen of the patch.

Various methods may be used to deliver the patch and the therapeutic factor. For, example, the patch may be compressed into a sheath than is delivered to a subject via a femoral artery. Once the end of the sheath is located to the vessel adjacent to the cardiac infarction, the patch is expelled from the sheath and placed by a balloon or similar structure, in an analogous to devices used to deploy stents.

Example 7A: Addition of Labels Such as Metal and/or Fluorescent Nanoparticles

Further, the patch may be treated to carry labels. These may include both magnetic and fluorescent labels, giving a bimodal imaging capability for the clinical applications. One may add superparamagnetic particles or nanoparticles to the collagen material during the preparation. Exemplary materials are described in US 20110206619, "Gold coated super paramagnetic iron oxide nano-particles (SPIONs) and a method of synthesizing the same". One may also add fluorescent microspheres or quantum dots, as commercially available, e.g. FluoSpheres™ from Life Technologies. The product can be monitored in vivo via MRI and/or fluorescence imaging systems. These characteristics are added to the patch by incorporating functionalized superparamagnetic iron nanoparticles (SPIONs) into the patch. Traditional tissue engineering patches do not have such capability and are completely invisible/untraceable following implantation in the patient's body (blind treatment). The ability to track the patch post implantation can be quite crucial in terms of monitoring the position, integration, and degradation of the patch in the patient body over the time.

The patch may also contain "antibacterial" properties. The nanoparticles mentioned above (SPIONs) will also give a significant antibacterial characteristic to this patch which makes the large scale, industrial production of this device much more feasible and easier. Again, the nanoparticles may be mixed into the collagen while it exists in a liquid or slurry state. For example, silver nanoparticles have been shown to have antimicrobial effects. Iron nanoparticles may also be used for antimicrobial effect. See Hajipour et al., "Antibacterial properties of nanoparticles", Trends in Biotechnology, 31(1) 61-2, and Mandy et al., "Antimicobial activity of zero-valent iron nanoparticles," International Journal of Modern Engineering Research (IJMER) 2(1) 578-581 (2012). As described there, metal oxide nanoparticles locally destroy bacteria. SPION particles may be used as antibacterial agents, as well as carboxy-grafted SPIONs, APTES-grafted SPIONs, Ag-coated SPIONs, and Au-coated SPIONs.

Example 8: Efficacy of FSTL1 Delivery

In order determine the optimum delivery, one may experiment with ischemia-reperfusion and permanent occlusion models, and then measuring the proliferative and/or protective effects. Both distal (e.g. cell division and survival) and proximal (e.g. molecular markers) as endpoints are used. Thus, exemplary experiments are summarized in Table 3. Anillin-GFP mouse models, as described above, are be conducted either by permanent LAD-occluded or schemia/reperfused. In both models delivery is performed either systemically (purified protein, as previously described) or FSTL1-loaded patch as the indicated times.

TABLE 3

Synopsis of animals and procedures

| Delivery | Injury | Delivery Time | n |
|---|---|---|---|
| FSTLI patch | LAD I/R | 0, 7, or 21 days after injury | 30 |
| FSTL1 systemic | Same | Same | 30 |
| Patch-only | Same | Same | 30 |
| Patch-only + FSTLI systemic | Same | Same | 30 |
| Sham | None | None | 10 |
| LAD | LAD | None | 10 |
| I/R | I/R | None | 10 |

Example 9: Synergy Between the Epicardial Biomaterial Patch and FSTL1

It is conceivable that the addition of the biomaterial itself enhances the beneficial properties of FSTL1 therefore, and improved effect of the local delivery might not be due to a niche generation, but to the synergy of two independent effects: biochemical (FSTL1) and biophysics (elastic properties provided by the patch). This possibility may be tested by combining system delivery of the purified protein with the implantation of an "empty" collagen patch. Times of delivery of patch and protein are simultaneous and at different times after injury, as in the previous experimental animals. Various FSLT1-patches are prepares and tested for the detection of anillin in the mid-body of faintly positive α-actinin cells in the myocardium of FSTL1patch mice. A patch prepared with different collagen plastic compression conditions. A method to engineer a 3D dense collagen patch that mimics the structural properties of the epicardium has been published by the present inventions in Serpooshan V, Zhao M, Metzler S A, Wei K, Shah P B, Wang A, et al. The effect of bioengineered acellular collagen patch on cardiac remodeling and ventricular function post myocardial infarction. Biomaterials. 2013; 34(36):9048-55, and is described above. Briefly, collagen gels are subjected to plastic compression via the application of a static compressive stress of ~700 Pa to the cast gel. This created a matrix with an elastic modulus measured by atomic force microscopy in the range of E~1-10 kPa. The optimum range can be fine-tuned as described here. The optimal range for supporting the contractile work and development of immature cardiomyocytes can be determined based on the particular collagen used, as described here. The reported elasticity that supports maximal cardiomyocyte work covers a range of about 1 to 11 E (kPa) the engineered scaffold is at about 5-7 E (kPa), and is close to the measured value for embryonic epicardium. (E=12±4 kPa), and somewhat less than that for neonatal and mature epicardium (E>30-40 kP.

Example 10: Treatment in Large Animals

Figures 17A, 17B, 17C:
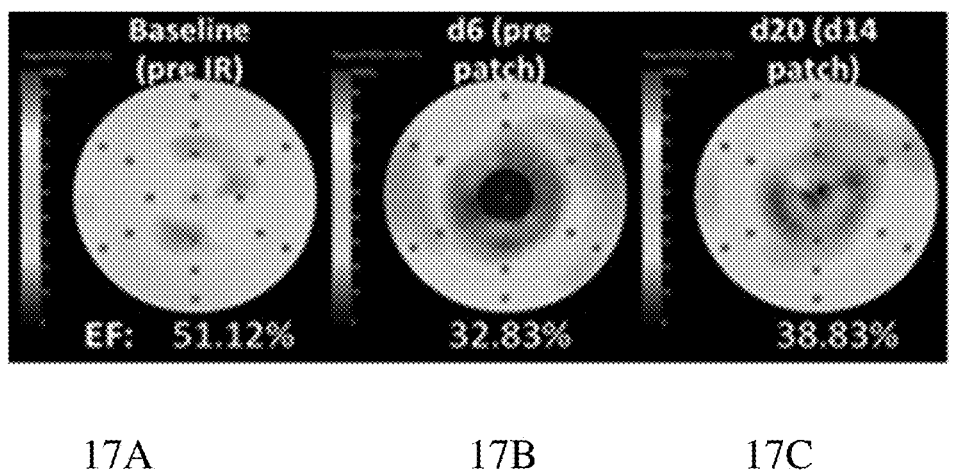

We have done a new series of pre-clinical studies by applying the patch in the pigs which suffer from ischemia/reperfusion injury. This is a very common model of heart injuries in human patients. The patch has significantly improved cardiac function in the treated pig hearts, 2 and 4 weeks post treatment were tested the efficacy of a FSTL1-loaded patch at long term I/R in 3 pigs. The experiment at day 14 after patch implantation shows a significant improvement of contractility, recovering already a 6% ejection fraction as displayed by MRI (FIG. 17A, B, C). 51% of left ventricular ejection fraction (EF) at baseline (pre IR) is the normal value for pig. EF decreased to 32.83% by IR at day 6, and improved 6% at day 20, 14 days from patch placement.

The patches were laden with FSTL1 (10 ng/ml) prepared with the above-described plastic compression method, having the above stiffness of consistent of stiffness consistent with contractility of normal myocardium, ranging from 1 to 10 kPa.

CONCLUSION

The above specific description is meant to exemplify and illustrate the invention and should not be seen as limiting the scope of the invention, which is defined by the literal and equivalent scope of the appended claims. Any patents or publications mentioned in this specification are indicative of levels of those skilled in the art to which the patent or publication pertains as of its date and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material to which is referred.

What is claimed is:

1. A composition for implantation into myocardium, comprising:
   (a) a scaffold comprising a cell-free collagenous material comprising a dense lamella between 100 and 300 μm in thickness and having a stiffness consistent with contractility of normal myocardium, ranging in stiffness from 1 to 10 kPa; and
   (b) one or more factors secreted by epicardial cells, wherein the one or more factors are present on or in the scaffold in an amount sufficient to promote regeneration of heart tissue,
   wherein the composition does not comprise cardiac type cells.

2. The composition of claim 1, further comprising a nanoparticle label within the collagenous material.

3. The composition of claim 1, wherein the one or more factors are selected from the group consisting of: Igfbp2 (Insulin-like growth factor-binding protein 2), Prss 1 (Anionic trypsin-1), C/u (Clusterin), Fstl1 (Follistatin-like 1 protein) peptide, Ogn (osteoglycin), Timp2 (Metalloproteinase inhibitor 2), Pxdn (peroxidasin), Sparc (SPARC, osteonectin), C1r (complement C1r subcomponent), Igfbp7 (Insulin-like growth factor binding protein 7), Olfml3 (olfactomedin-like 3), Metrnl (Meteorin-like protein), Serpinf1 (Serine (Or cysteine) peptidase inhibitor, clade F, member 1), Bmp1 (bone morphogenetic protein 1), Pdgfa (Platelet-derived growth factor subunit A), and Crip2 (Cysteine-rich protein 2).

4. The composition of claim 3, wherein the Fstl1 peptide is follistatin-like1 protein (Fstl-1).

5. The composition of claim 3, wherein the one or more factors comprises at least two of the factors.

6. The composition of claim 1, wherein the one or more factors consists essentially of purified follistatin-like1 (fstl-1) peptide.

7. The composition of claim 1, wherein the collagenous material contains fluorescent labels.

8. The composition of claim 1, wherein the collagenous material is selected from the group consisting of: rat collagen, bovine collagen, porcine collagen, human collagen, and human type I collagen.

9. The composition of claim 1, wherein the thin dense lamella is at a bottom portion of the collagenous material and a layer of hydrated material is attached at a top portion of the collagenous material.

10. A method for promoting regeneration of heart tissue, comprising:
    implanting the composition of claim 1 into heart tissue in the vicinity of an infarction in the heart tissue, thereby promoting the regeneration of heart tissue.

11. The method of claim 10, wherein the one or more factors are selected from the group consisting of: fstl1 peptide, and Igfbp2 (Insulin-like growth factor-binding protein 2) peptide.

12. The method of claim 10, wherein the one or more factors comprise purified follistatin-like1 protein (fstl-1) peptide.

13. The method of claim 10, wherein the composition further comprises a nanoparticle which is one or more of a fluorescent nanoparticle and a metal nanoparticle.

14. The method of claim 13, wherein the nanoparticle is a coated super paramagnetic iron oxide nanoparticle.

15. The composition of claim 1, wherein the one or more factors comprises recombinant follistatin-like1 protein (Fstl-1).

16. A composition for implantation into myocardium, comprising:
   (a) a scaffold comprising a cell-free collagenous material comprising a dense lamella between 100 and 300 μm in thickness and having a stiffness consistent with contractility of normal myocardium, ranging in stiffness from 1 to 25 kPa; and
   (b) one or more factors secreted by epicardial cells, wherein the one or more factors are present on or in the scaffold in an amount sufficient to promote regeneration of heart tissue,
   wherein the composition does not comprise cardiac type cells.

* * * * *

SEQUENCE LISTING

```
<160> NUMBER OF SEQ ID NOS: 9

<210> SEQ ID NO 1
<211> LENGTH: 308
<212> TYPE: PRT
<213> ORGANISM: Homo sapiens

<400> SEQUENCE: 1

Met Trp Lys Arg Trp Leu Ala Leu Ala Leu Val Ala Val Ala
1               5                   10                  15

Trp Val Arg Ala Glu Glu Glu Leu Arg Ser Lys Ser Lys Ile Cys Ala
                20                  25                  30

Asn Val Phe Cys Gly Ala Gly Arg Glu Cys Ala Val Thr Glu Lys Gly
            35                  40                  45

Glu Pro Thr Cys Leu Cys Ile Glu Gln Cys Lys Pro His Lys Arg Pro
        50                  55                  60

Val Cys Gly Ser Asn Gly Lys Thr Tyr Leu Asn His Cys Glu Leu His
65                  70                  75                  80

Arg Asp Ala Cys Leu Thr Gly Ser Lys Ile Gln Val Asp Tyr Asp Gly
                85                  90                  95

His Cys Lys Glu Lys Lys Ser Val Ser Pro Ser Ala Ser Pro Val Val
            100                 105                 110

Cys Tyr Gln Ser Asn Arg Asp Glu Leu Arg Arg Arg Ile Ile Gln Trp
        115                 120                 125

Leu Glu Ala Glu Ile Ile Pro Asp Gly Trp Phe Ser Lys Gly Ser Asn
    130                 135                 140

Tyr Ser Glu Ile Leu Asp Lys Tyr Phe Lys Asn Phe Asp Asn Gly Asp
145                 150                 155                 160

Ser Arg Leu Asp Ser Ser Glu Phe Leu Lys Phe Val Glu Gln Asn Glu
                165                 170                 175

Thr Ala Ile Asn Ile Thr Thr Tyr Pro Asp Gln Glu Asn Asn Lys Leu
```

```
                180                 185                 190
Leu Arg Gly Leu Cys Val Asp Ala Leu Ile Glu Leu Ser Asp Glu Asn
            195                 200                 205

Ala Asp Trp Lys Leu Ser Phe Gln Glu Phe Leu Lys Cys Leu Asn Pro
    210                 215                 220

Ser Phe Asn Pro Pro Glu Lys Lys Cys Ala Leu Glu Asp Glu Thr Tyr
225                 230                 235                 240

Ala Asp Gly Ala Glu Thr Glu Val Asp Cys Asn Arg Cys Val Cys Ala
                245                 250                 255

Cys Gly Asn Trp Val Cys Thr Ala Met Thr Cys Asp Gly Lys Asn Gln
            260                 265                 270

Lys Gly Ala Gln Thr Gln Thr Glu Glu Met Thr Arg Tyr Val Gln
        275                 280                 285

Glu Leu Gln Lys His Gln Glu Thr Ala Glu Lys Thr Leu Arg Val Ser
            290                 295                 300

Thr Lys Glu Ile
305

<210> SEQ ID NO 2
<211> LENGTH: 18
<212> TYPE: DNA
<213> ORGANISM: Artificial
<220> FEATURE:
<223> OTHER INFORMATION: GAPDH forward primer

<400> SEQUENCE: 2
aatggatacg gctacagc                                                   18

<210> SEQ ID NO 3
<211> LENGTH: 18
<212> TYPE: DNA
<213> ORGANISM: Artificial
<220> FEATURE:
<223> OTHER INFORMATION: GAPDH reverse primer

<400> SEQUENCE: 3
gtgcagcgaa ctttattg                                                   18

<210> SEQ ID NO 4
<211> LENGTH: 17
<212> TYPE: DNA
<213> ORGANISM: Artificial
<220> FEATURE:
<223> OTHER INFORMATION: Myh6 forward primer

<400> SEQUENCE: 4
catgccaatg acgacct                                                    17

<210> SEQ ID NO 5
<211> LENGTH: 19
<212> TYPE: DNA
<213> ORGANISM: Artificial
<220> FEATURE:
<223> OTHER INFORMATION: Myh6 reverse primer

<400> SEQUENCE: 5
cctacactcc tgtactgcc                                                  19

<210> SEQ ID NO 6
<211> LENGTH: 21
<212> TYPE: DNA
<213> ORGANISM: Artificial
```

```
<220> FEATURE:
<223> OTHER INFORMATION: Mlc2v forward primer

<400> SEQUENCE: 6
aggtccaatt aacttcaccg t                                              21

<210> SEQ ID NO 7
<211> LENGTH: 20
<212> TYPE: DNA
<213> ORGANISM: Artificial
<220> FEATURE:
<223> OTHER INFORMATION: Mlc2v reverse primer

<400> SEQUENCE: 7
gtcagcatct cccggacata                                                20

<210> SEQ ID NO 8
<211> LENGTH: 17
<212> TYPE: DNA
<213> ORGANISM: Artificial
<220> FEATURE:
<223> OTHER INFORMATION: Mlc2a forward primer

<400> SEQUENCE: 8
accgtcttcc tcacact                                                   17

<210> SEQ ID NO 9
<211> LENGTH: 17
<212> TYPE: DNA
<213> ORGANISM: Artificial
<220> FEATURE:
<223> OTHER INFORMATION: Mlc2a reverse primer

<400> SEQUENCE: 9
cttgtctgcc tgggtca                                                   17
```